(12) United States Patent
Tally et al.

(10) Patent No.: US 12,161,538 B2
(45) Date of Patent: *Dec. 10, 2024

(54) ABSORBENT ARTICLES HAVING FULLY REMOVABLE FASTENING MEMBERS

(71) Applicant: The Procter & Gamble Company, Cincinnati, OH (US)

(72) Inventors: Amy L. Tally, Cold Spring, KY (US); Susan J. Ludwig, West Chester, OH (US); Donald C. Roe, West Chester, OH (US); Ronald J. Zink, Blue Ash, OH (US); Jennifer J. Gustin, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/216,631

(22) Filed: Jun. 30, 2023

(65) Prior Publication Data

US 2023/0338203 A1 Oct. 26, 2023

Related U.S. Application Data

(63) Continuation of application No. 16/789,524, filed on Feb. 13, 2020, now Pat. No. 11,730,633.

(Continued)

(51) Int. Cl.
*A61F 13/49* (2006.01)
*A61F 13/511* (2006.01)
*A61F 13/514* (2006.01)

(52) U.S. Cl.
CPC .. *A61F 13/49004* (2013.01); *A61F 13/49001* (2013.01); *A61F 13/49061* (2013.01);

(Continued)

(58) Field of Classification Search
CPC .......... A61F 13/49001; A61F 13/49004; A61F 13/49061; A61F 13/5622; A61F 13/5638;

(Continued)

(56) References Cited

U.S. PATENT DOCUMENTS 3,799,167 A   3/1974 Miller et al.
3,800,796 A * 4/1974 Jacob ..................... A61F 13/58
                                                     604/369

(Continued)

FOREIGN PATENT DOCUMENTS

CN   101242796 A   8/2008
CN   102217995 A   10/2011

(Continued)

OTHER PUBLICATIONS

"Beary Small Bili-Buns Phototherapy Diapers", http://www.small-beginnings.com, No Known Date, 4 pages.

(Continued)

*Primary Examiner* — Michele Kidwell
(74) *Attorney, Agent, or Firm* — Daniel S. Albrecht

(57) ABSTRACT

An absorbent article includes a topsheet, a backsheet, and an absorbent core positioned at least partially intermediate the topsheet and the backsheet. The absorbent article includes a first waist region, a second waist region, and a fully removable fastening member configured to join a portion of the first waist region to the second waist region. The fastening member includes a first end region comprising a first end, a second end region comprising a second end, a first fastener on a first surface of the fastening member and in the first end region, and a second fastener on the first surface and in the second end region. The fastening member includes a grasp region either partially laterally outboard of the first fastener or laterally outboard of the first fastener in the first end (Continued)

region. The grasp region has a different physical property than a remainder of the fastening member.

20 Claims, 28 Drawing Sheets

Related U.S. Application Data

(60) Provisional application No. 62/808,352, filed on Feb. 21, 2019.

(52) U.S. Cl.
CPC ............ *A61F 2013/49033* (2013.01); *A61F 2013/4905* (2013.01); *A61F 2013/51178* (2013.01); *A61F 2013/51411* (2013.01); *A61F 2013/51452* (2013.01)

(58) Field of Classification Search
CPC ........ A61F 13/5644; A61F 2013/49033; A61F 2013/4905; A61F 2013/51411; A61F 2013/51452; A61F 13/56; A61F 13/64; A61F 13/66
See application file for complete search history.

(56) References Cited

U.S. PATENT DOCUMENTS

| | | |
|---|---|---|
| 4,257,418 A | 3/1981 | Hessner |
| 4,315,508 A | 2/1982 | Bolick et al. |
| 4,561,102 A | 12/1985 | Prezas |
| 4,661,102 A | 4/1987 | Shikata et al. |
| 5,026,364 A | 6/1991 | Robertson |
| 5,147,345 A | 9/1992 | Lavon |
| 5,149,720 A | 9/1992 | Desmarais et al. |
| 5,374,262 A | 12/1994 | Keuhn, Jr. et al. |
| 5,386,595 A | 2/1995 | Kuen et al. |
| H001440 H | 5/1995 | New |
| 5,624,429 A | 4/1997 | Long et al. |
| 5,653,842 A | 8/1997 | Kuen |
| 5,669,901 A | 9/1997 | Lafortune et al. |
| 5,702,377 A | 12/1997 | Collier, IV et al. |
| 5,795,921 A | 8/1998 | Dyer et al. |
| 5,827,259 A | 10/1998 | Laux |
| 5,827,909 A | 10/1998 | Desmarais |
| 5,843,066 A | 12/1998 | Dobrin |
| 5,869,171 A | 2/1999 | Shiveley et al. |
| 5,906,604 A | 5/1999 | Roennberg et al. |
| 5,931,827 A | 8/1999 | Buell et al. |
| 5,934,470 A | 8/1999 | Bauer et al. |
| 5,938,652 A | 8/1999 | Sauer |
| 5,971,970 A | 10/1999 | Carlbark et al. |
| 5,993,433 A | 11/1999 | St. Louis |
| 6,010,490 A | 1/2000 | Freeland et al. |
| 6,010,491 A | 1/2000 | Roe et al. |
| 6,120,486 A | 9/2000 | Toyoda et al. |
| 6,132,410 A | 10/2000 | Van Gompel et al. |
| 6,132,411 A * | 10/2000 | Huber .............. A61F 13/49015 604/389 |
| 6,135,988 A | 10/2000 | Turner et al. |
| 6,174,303 B1 | 1/2001 | Suprise et al. |
| 6,217,563 B1 | 4/2001 | Van Gompel et al. |
| 6,315,764 B1 | 11/2001 | Faulks et al. |
| 6,336,922 B1 | 1/2002 | Vangompel et al. |
| 6,365,642 B1 | 4/2002 | Dyer et al. |
| 6,369,121 B1 | 4/2002 | Catalfamo et al. |
| 6,371,950 B1 | 4/2002 | Roslansky et al. |
| 6,432,099 B2 | 8/2002 | Roennberg |
| 6,491,677 B1 | 12/2002 | Glaug et al. |
| 6,520,947 B1 | 2/2003 | Tilly et al. |
| 6,626,880 B2 | 9/2003 | Onishi |
| 6,627,786 B2 | 9/2003 | Roe et al. |
| 6,638,262 B2 | 10/2003 | Suzuki et al. |
| 6,659,993 B2 | 12/2003 | Minato |
| 6,767,344 B2 | 7/2004 | Suzuki |
| 6,790,203 B2 | 9/2004 | Een |
| 6,817,993 B1 | 11/2004 | Simmons et al. |
| 6,911,407 B2 | 6/2005 | Sherrod et al. |
| 6,921,394 B2 | 7/2005 | Sayama et al. |
| 7,118,557 B2 | 10/2006 | Minato et al. |
| 7,163,530 B1 | 1/2007 | Toyoshima et al. |
| 7,419,562 B2 | 9/2008 | Van Gompel |
| 7,670,324 B2 | 3/2010 | Young et al. |
| 7,753,899 B2 | 7/2010 | Mori et al. |
| 7,785,309 B2 | 8/2010 | Van Gompel et al. |
| 7,879,017 B1 | 2/2011 | Tabata |
| 8,181,278 B2 | 5/2012 | Odorzynski et al. |
| 8,216,201 B2 | 7/2012 | Beck |
| 8,231,592 B2 | 7/2012 | Suzuki et al. |
| 8,430,858 B2 | 4/2013 | Baeck |
| 8,449,518 B2 | 5/2013 | Allison-rogers |
| 8,668,680 B2 | 3/2014 | Ichikawa et al. |
| 8,734,419 B2 | 5/2014 | Ormsby |
| 8,747,380 B2 | 6/2014 | Coates |
| 8,764,721 B2 | 7/2014 | Van Gompel |
| 8,764,722 B2 | 7/2014 | Rhein et al. |
| 8,821,467 B1 | 9/2014 | Minella |
| 8,894,626 B2 | 11/2014 | Beck |
| 8,926,580 B2 | 1/2015 | Carney et al. |
| 8,979,815 B2 | 3/2015 | Roe et al. |
| 8,992,496 B2 | 3/2015 | Bäck |
| 9,044,358 B2 | 6/2015 | Nakajima et al. |
| 9,168,181 B2 | 10/2015 | Popp et al. |
| 9,216,116 B2 | 12/2015 | Roe et al. |
| 9,216,118 B2 | 12/2015 | Roe et al. |
| 9,259,362 B2 | 2/2016 | Popp et al. |
| 9,445,951 B2 | 9/2016 | Moberg-alehammar et al. |
| 9,554,952 B2 | 1/2017 | Rönnberg et al. |
| 9,597,238 B2 | 3/2017 | Joseph et al. |
| 9,789,009 B2 | 10/2017 | Joseph |
| 9,867,412 B2 | 1/2018 | Hansson et al. |
| 11,452,646 B2 | 9/2022 | Tally |
| 11,730,633 B2 * | 8/2023 | Tally ................ A61F 13/49004 604/391 |
| 2002/0016579 A1 | 2/2002 | Stenberg |
| 2002/0111596 A1 | 8/2002 | Fletcher |
| 2002/0120248 A1 | 8/2002 | Onishi et al. |
| 2002/0138054 A1 | 9/2002 | Erdman |
| 2003/0050616 A1 | 3/2003 | Reynolds et al. |
| 2004/0023171 A1 | 2/2004 | Weimann et al. |
| 2004/0102757 A1 | 5/2004 | Olson |
| 2004/0127867 A1 | 7/2004 | Odorzynski et al. |
| 2004/0230171 A1 | 11/2004 | Ando |
| 2005/0222546 A1 | 10/2005 | Vargo |
| 2006/0142729 A1 | 6/2006 | Sivilich et al. |
| 2006/0247597 A1 | 11/2006 | Hogan et al. |
| 2007/0049895 A1 | 3/2007 | Van Gompel et al. |
| 2007/0102750 A1 | 5/2007 | Kim et al. |
| 2007/0232180 A1 | 10/2007 | Polat et al. |
| 2007/0233027 A1 | 10/2007 | Roe et al. |
| 2008/0065034 A1 | 3/2008 | Vargo et al. |
| 2008/0082072 A1 | 4/2008 | Helmfridsson et al. |
| 2009/0306616 A1 | 12/2009 | Wennerbaeck |
| 2010/0004616 A1 | 1/2010 | Nakamura et al. |
| 2010/0168695 A1 | 7/2010 | Robles |
| 2010/0234822 A1 | 9/2010 | Baeck |
| 2010/0274213 A1 | 10/2010 | Gustin et al. |
| 2011/0178486 A1 | 7/2011 | Beck et al. |
| 2011/0184372 A1 | 7/2011 | Esping |
| 2012/0116339 A1 | 5/2012 | Labit et al. |
| 2013/0090619 A1 | 4/2013 | Carbonari et al. |
| 2013/0110065 A1 | 5/2013 | Takahashi et al. |
| 2013/0261584 A1 | 10/2013 | Lee |
| 2013/0261585 A1 | 10/2013 | Lee |
| 2013/0261586 A1 | 10/2013 | Lee |
| 2013/0331807 A1 | 12/2013 | Ichihara et al. |
| 2014/0052086 A1 | 2/2014 | Komatsu et al. |
| 2014/0068839 A1 | 3/2014 | Steele et al. |
| 2014/0076183 A1 | 3/2014 | Rasch et al. |
| 2014/0107605 A1 | 4/2014 | Schroer, Jr. |
| 2014/0135724 A1 | 5/2014 | Robles et al. |
| 2014/0142528 A1 | 5/2014 | Wang et al. |
| 2014/0142529 A1 | 5/2014 | Cheng |

(56) References Cited

U.S. PATENT DOCUMENTS

| | | |
|---|---|---|
| 2014/0155856 A1 | 6/2014 | Ronnberg et al. |
| 2014/0163501 A1 | 6/2014 | Ehrnsperger et al. |
| 2014/0221956 A1 | 8/2014 | Martynus et al. |
| 2014/0257227 A1 | 9/2014 | Roe |
| 2014/0303589 A1 | 10/2014 | Paz et al. |
| 2014/0336606 A1 | 11/2014 | Bewick-sonntag et al. |
| 2014/0345034 A1 | 11/2014 | Hansson et al. |
| 2014/0350508 A1 | 11/2014 | Popp |
| 2014/0375297 A1 | 12/2014 | Geiger et al. |
| 2015/0065973 A1 | 3/2015 | Roe et al. |
| 2015/0065975 A1 | 3/2015 | Roe |
| 2015/0182389 A1 | 7/2015 | Takino |
| 2015/0250662 A1 | 9/2015 | Isele et al. |
| 2015/0282997 A1 | 10/2015 | Arizti |
| 2016/0038628 A1 | 2/2016 | Klofta et al. |
| 2016/0136002 A1 | 5/2016 | Chandrasekaran et al. |
| 2016/0136014 A1 | 5/2016 | Arora |
| 2017/0027776 A1 | 2/2017 | Matsuda et al. |
| 2017/0095378 A1* | 4/2017 | Sheehan ........... A61F 13/49011 |
| 2017/0151103 A1 | 6/2017 | Bianchi |
| 2017/0246043 A1 | 8/2017 | Ludwig |
| 2017/0246044 A1 | 8/2017 | Ludwig |
| 2017/0246052 A1 | 8/2017 | Ludwig |
| 2017/0252015 A1 | 9/2017 | Barnhorst |
| 2017/0252233 A1 | 9/2017 | Barnhorst |
| 2018/0344544 A1 | 12/2018 | Tally |
| 2019/0060130 A1 | 2/2019 | Tally et al. |
| 2019/0374397 A1 | 12/2019 | Tally et al. |
| 2020/0268566 A1 | 8/2020 | Tally et al. |
| 2022/0362076 A1 | 11/2022 | Tally |

FOREIGN PATENT DOCUMENTS

| | | |
|---|---|---|
| CN | 202027809 U | 11/2011 |
| CN | 202191413 U | 4/2012 |
| CN | 202207245 U | 5/2012 |
| CN | 202288655 U | 7/2012 |
| CN | 202515884 U | 11/2012 |
| CN | 102958479 A | 3/2013 |
| CN | 202801952 U | 3/2013 |
| CN | 204709180 U | 10/2015 |
| CN | 204932009 U | 1/2016 |
| CN | 106726167 A | 5/2017 |
| CN | 206342616 U | 7/2017 |
| DE | 3810473 A1 | 10/1989 |
| DE | 102011007818 A1 | 10/2012 |
| DE | 102011007821 A1 | 10/2012 |
| EP | 0925769 A2 | 6/1999 |
| GB | 2080093 A | 2/1982 |
| JP | 2000508930 A | 7/2000 |
| JP | 2003175066 A | 6/2003 |
| JP | 2004195083 A | 7/2004 |
| JP | 2005304605 A | 11/2005 |
| JP | 2009082484 A | 4/2009 |
| JP | 2010227508 A | 10/2010 |
| JP | 2011072657 A | 4/2011 |
| JP | 2011072659 A | 4/2011 |
| JP | 2011098032 A | 5/2011 |
| JP | 2011136063 A | 7/2011 |
| JP | 2011172793 A | 9/2011 |
| JP | 2012110539 A | 6/2012 |
| JP | 2013255841 A | 12/2013 |
| JP | 5690966 B1 | 2/2015 |
| JP | 2015202200 A | 11/2015 |
| JP | 2016030200 A | 3/2016 |
| JP | 2016030201 A | 3/2016 |
| JP | 2016030202 A | 3/2016 |
| JP | 5934815 B1 | 5/2016 |
| JP | 3205471 B2 | 7/2016 |
| JP | 2016146986 A | 8/2016 |
| TW | 201626969 A | 8/2016 |
| WO | 0059430 A1 | 10/2000 |
| WO | 0101907 A1 | 1/2001 |
| WO | 2010020990 A2 | 2/2010 |
| WO | 2012143227 A1 | 10/2012 |
| WO | 2012143228 A1 | 10/2012 |
| WO | 2012143230 A1 | 10/2012 |
| WO | 2012145964 A1 | 11/2012 |
| WO | 2015046632 A1 | 4/2015 |
| WO | 2015182179 A1 | 12/2015 |
| WO | 2016013258 A1 | 1/2016 |
| WO | 2016013662 A1 | 1/2016 |
| WO | 2016013663 A1 | 1/2016 |
| WO | 2016104148 A1 | 6/2016 |
| WO | 2016121183 A1 | 8/2016 |
| WO | 2016121236 A1 | 8/2016 |
| WO | 2018099974 A1 | 6/2018 |

OTHER PUBLICATIONS

15460 PCT Search Report and Written Opinion PCT/US2020/018025 dated Jun. 9, 2020, 10 pages.
All Office Actions; U.S. Appl. No. 15/993,967, filed May 31, 2018.
All Office Actions; U.S. Appl. No. 16/789,524, filed Feb. 13, 2020.
All Office Actions; U.S. Appl. No. 17/874,417, filed Jul. 27, 2022.

* cited by examiner

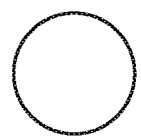
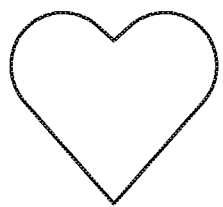
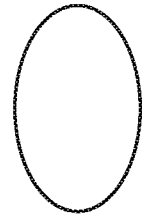
FIG. 28	FIG. 29	FIG. 30
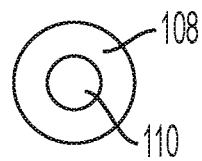
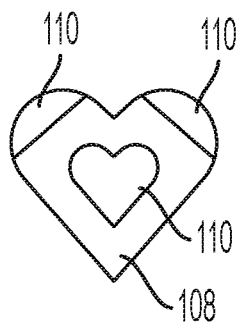
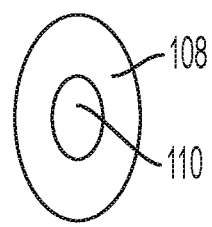
FIG. 31	FIG. 32	FIG. 33
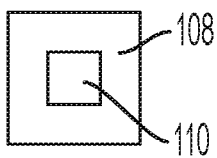
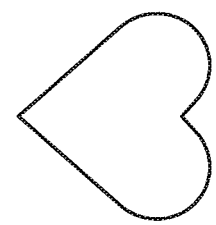
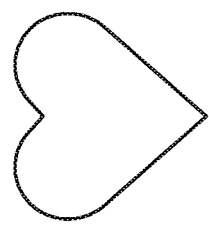
FIG. 34	FIG. 35	FIG. 36

ABSORBENT ARTICLES HAVING FULLY REMOVABLE FASTENING MEMBERS

CROSS REFERENCE TO RELATED APPLICATIONS

This application is a continuation of U.S. application Ser. No. 16/789,524, filed on Feb. 13, 2020, which claims the benefit, under 35 U.S.C. § 119(e), of U.S. Provisional Patent Application Ser. No. 62/808,352, filed on Feb. 21, 2019, the entire disclosure of which is incorporated by reference herein.

FIELD

The present disclosure is generally directed to absorbent articles comprising fully removable fastening members and, is more particularly directed to, absorbent articles comprising fully removable fastening members with grasp regions and/or one or more curvilinear portions.

BACKGROUND

Absorbent articles are used to contain and absorb bodily exudates (i.e., urine, bowel movements, and menses) in infants, children, and adults. Absorbent articles may be used in hospitals for diapering infants, premature babies, and/or Neonatal Abstinence Syndrome ("NAS") babies. Premature babies, NAS babies, or other small infants may require special care by nurses and/or other hospital staff. In instances of high risk and earlier born premature babies, the babies may be at risk for developmental delays. Premature birth may interrupt rapid growth in the brain that occurs in the third trimester of a pregnancy. Due to immaturity, premature babies may be at risk for both neurological and physiological impairment. As part of the care to promote proper body mechanics and skeletal development in these babies, positioning of preterm infants has become a basic neonatal nursing care practice. The positions include prone, supine, and side-lying positions. There have been several studies that have demonstrated a variety of improved outcomes affected by different positioning of premature infants. As an attempt to address the neurological development of these babies, it has become common practice to minimize stresses or stimuli in the neonatal intensive care unit ("NICU") to manage any negative influence. As part of this, practices to reduce handling of the babies in the NICU as well as supporting the increase of skin to skin contact are being recommended.

Premature or NAS babies may benefit from unconventional fastening system requirements, such as providing one or more fully removable fastening members having two or more fasteners on the same wearer-facing surface thereof. These fully removable fastening members may allow nurses or caregivers to perform a diaper change without having to reposition the baby as done during a regular diaper change. A used absorbent article may be removed and replaced without altering the position of the baby. When applying and removing the removable fastening members, it is important to note that the NICU environment is often dimly lit to minimize stimulation to the babies. Therefore, it may be important that the nurses can easily identify where the fasteners (e.g., hooks) are and be able to easily grip portions of the fastening members outboard of the fasteners for easy application and/or removal as to minimize the disturbance to the baby. Current removable fastening members do not provide such advantageous features, and regions outboard of the fasteners tend to be floppy, low basis weight, and not easy to grasp. As such, removable fastening members for absorbent articles should be improved to achieve faster and easier fastening member application and removal. Additionally, in a rectangular fastening member configuration, the nurses or caregivers are somewhat limited in how he or she can apply the fastening members to fit a certain wearer. Wearers are many different sizes and shapes. As such, removable fastening members for absorbent articles should be improved to provide more options for nurses or caregivers during application of the fastening members.

SUMMARY

The present disclosure provides absorbent articles with one or more fully removable fastening members, wherein the fastening members comprise grasp regions at least partially outboard of at least one of the fasteners (e.g., hooks) or laterally outboard of at least one of the fasteners. Such grasp regions may aid nurses or caregivers in easier fastening member application and/or removal during absorbent article changes or repositioning. The grasp regions may also enable nurses or caregivers to readily identify the location of the fasteners to enable fastening member removal and/or application and, thereby, faster and smoother absorbent article changes or repositioning. Faster and smoother absorbent article changes or repositioning may lead to less stress on the baby. The grasp regions may have a different physical property than a remainder of the fully removable fastening member in an area free of the fasteners. The physical property may be thickness, stiffness, texture, basis weight, and/or number of materials. The grasp regions may also have a different color than a remainder of the fastening members and/or the fasteners to allow nurses or caregivers to readily identify where to grasp. Texture in the grasp regions may also help nurses or caregivers identify where to grasp in low light situations.

Additionally, the present disclosure provides absorbent articles with one or more fully removable, shaped fastening members comprising fasteners (e.g., hooks) that provide nurses and caregivers with more customizable options for absorbent article fit. The fully removable shaped fastening members may have first and second side edges each with one or more curvilinear portions or one or more concave and/or convex portions. The fully removable fastening members may each have a central lateral axis. The first and second side edges may be symmetrical or asymmetrical to each other about the central lateral axis. Having shaped fastening members enables nurses or caregivers to choose the leg opening size and/or shape independently from the waist opening size. The waist opening size is dependent on where on the first and second waist regions of an absorbent article a nurse or caregiver chooses to affix ends of the fastening members. The nurse or caregiver may change the size and/or shape by 1) choosing where on a longitudinal length of the absorbent article to affix a fastener of the fastening member or 2) whether a concave or convex side of the fastening member is facing the wearer's thigh/leg (as opposed to facing the waist). For smaller wearers with smaller thighs/legs, facing the convex side toward the thigh/leg will make the leg opening smaller. For larger wearer with larger thighs/legs, facing the concave side toward the thigh/leg will make the leg opening larger. Combinations of convex and concave portions along the first and second fastening member side edges provides degrees of freedom for nurse or caregivers to quickly and effectively achieve the desired fit on the wearer on many sizes. End edges of the fastening members may also be shaped, comprise one or more curvilinear portions, and/or comprise one or more convex or concave portions.

BRIEF DESCRIPTION OF THE DRAWINGS

The above-mentioned and other features and advantages of the present disclosure, and the manner of attaining them, will become more apparent and the disclosure itself will be better understood by reference to the following description of example forms of the disclosure taken in conjunction with the accompanying drawings, wherein:

FIGS. 28-38 are plan views of shapes and/or configurations of fasteners for the fastening members;

DETAILED DESCRIPTION

Various non-limiting forms of the present disclosure will now be described to provide an overall understanding of the principles of the structure, function, manufacture, and use of the absorbent articles having fully removable fastening members disclosed herein. One or more examples of these non-limiting forms are illustrated in the accompanying drawings. Those of ordinary skill in the art will understand that the absorbent articles having fully removable fastening members described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

Initially, an example absorbent article that may be used with the fully removable fastening members will be described although it will be understood that the fully removable fastening members described herein may be used with any suitable type of diaper chassis. The example absorbent article illustrated in FIGS. 1-9 shows rectangular shaped fully removable fastening members as an example. It will be understood that any of the fully removable fastening members disclosed herein may be used with the example absorbent article or with other absorbent articles. For example, the fully removable fastening members may be shaped and/or comprise grasp regions.

Figure 1:
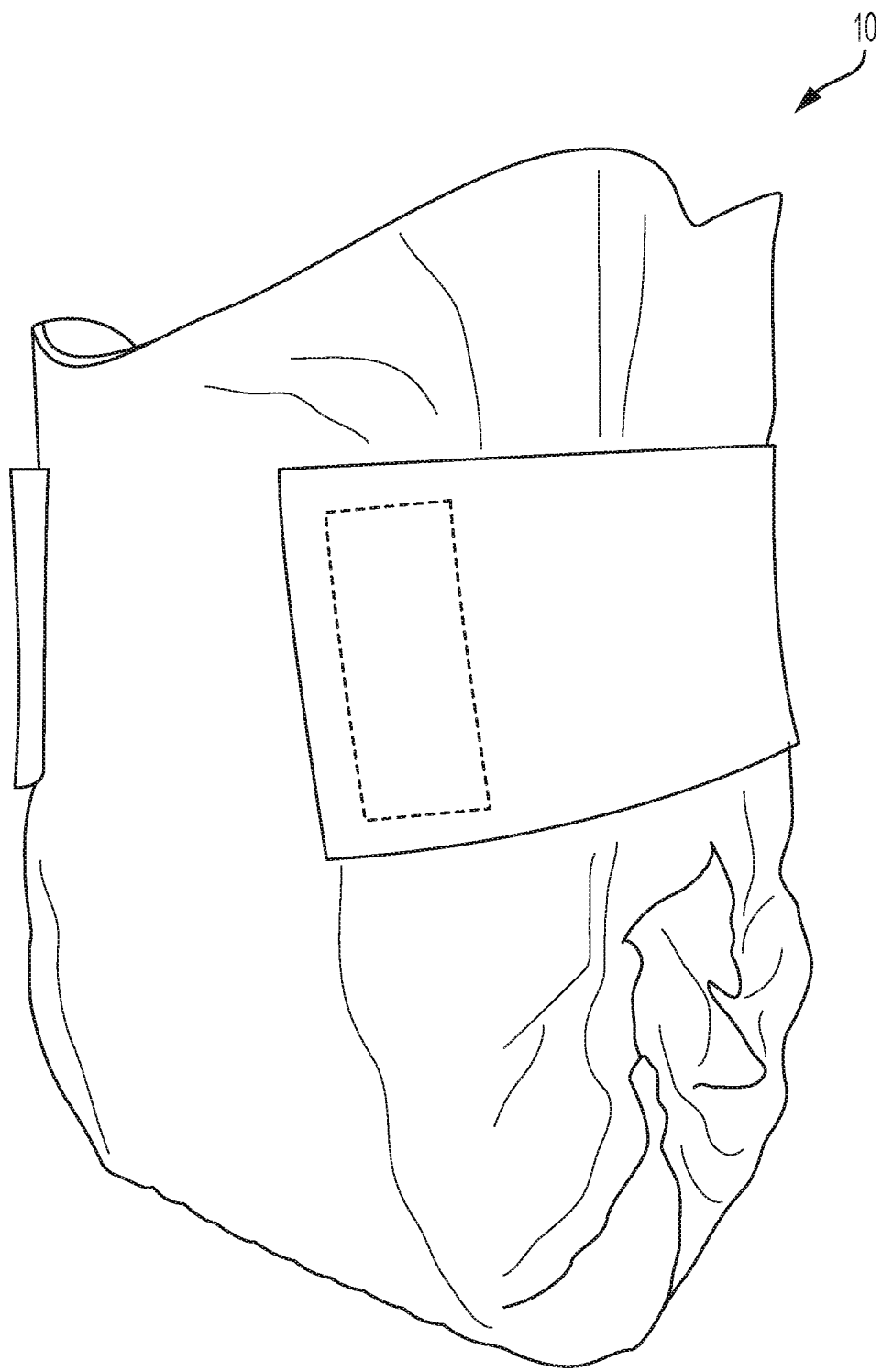
FIG. 1 is a front perspective view photograph of an absorbent article of the present disclosure in an in-use configuration.
Figure 2:
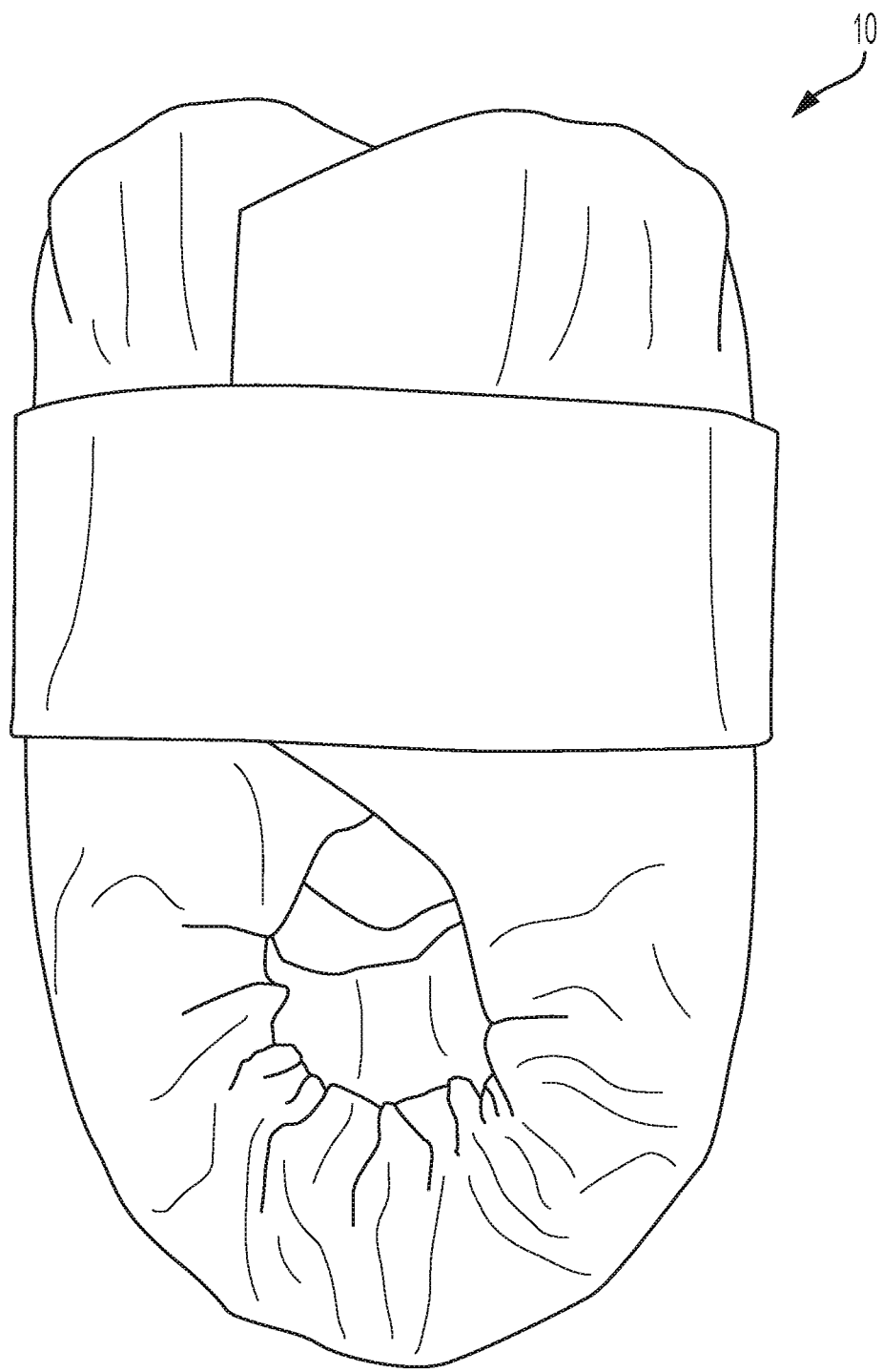
FIG. 2 is a side view photograph of the absorbent article of FIG. 1 in the in-use configuration.
Figure 3:
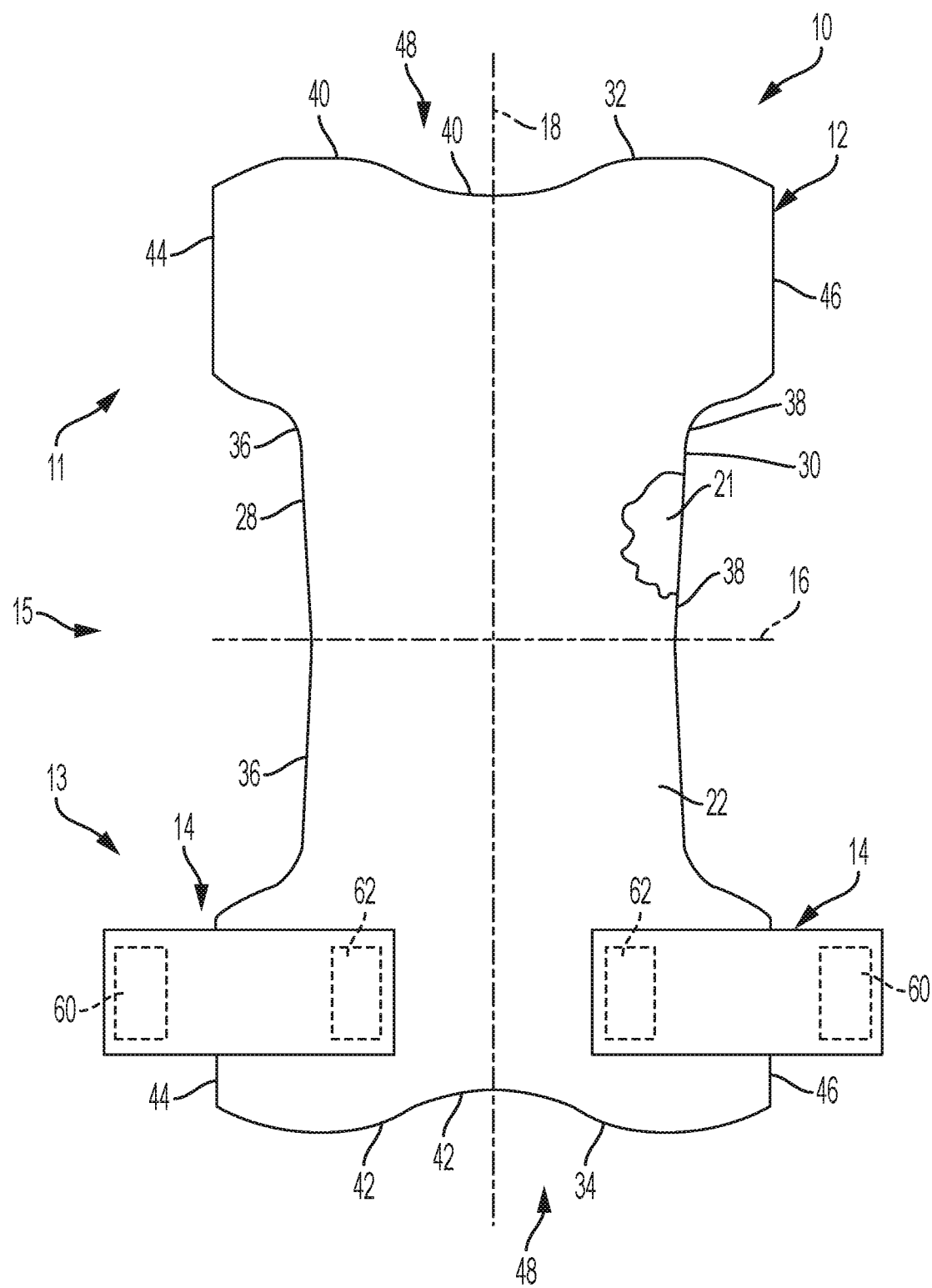
FIG. 3 is a plan view of an absorbent article of the present disclosure, garment-facing surface facing the viewer, and with removable fastening members attached to an outer cover nonwoven material.
Figure 4:
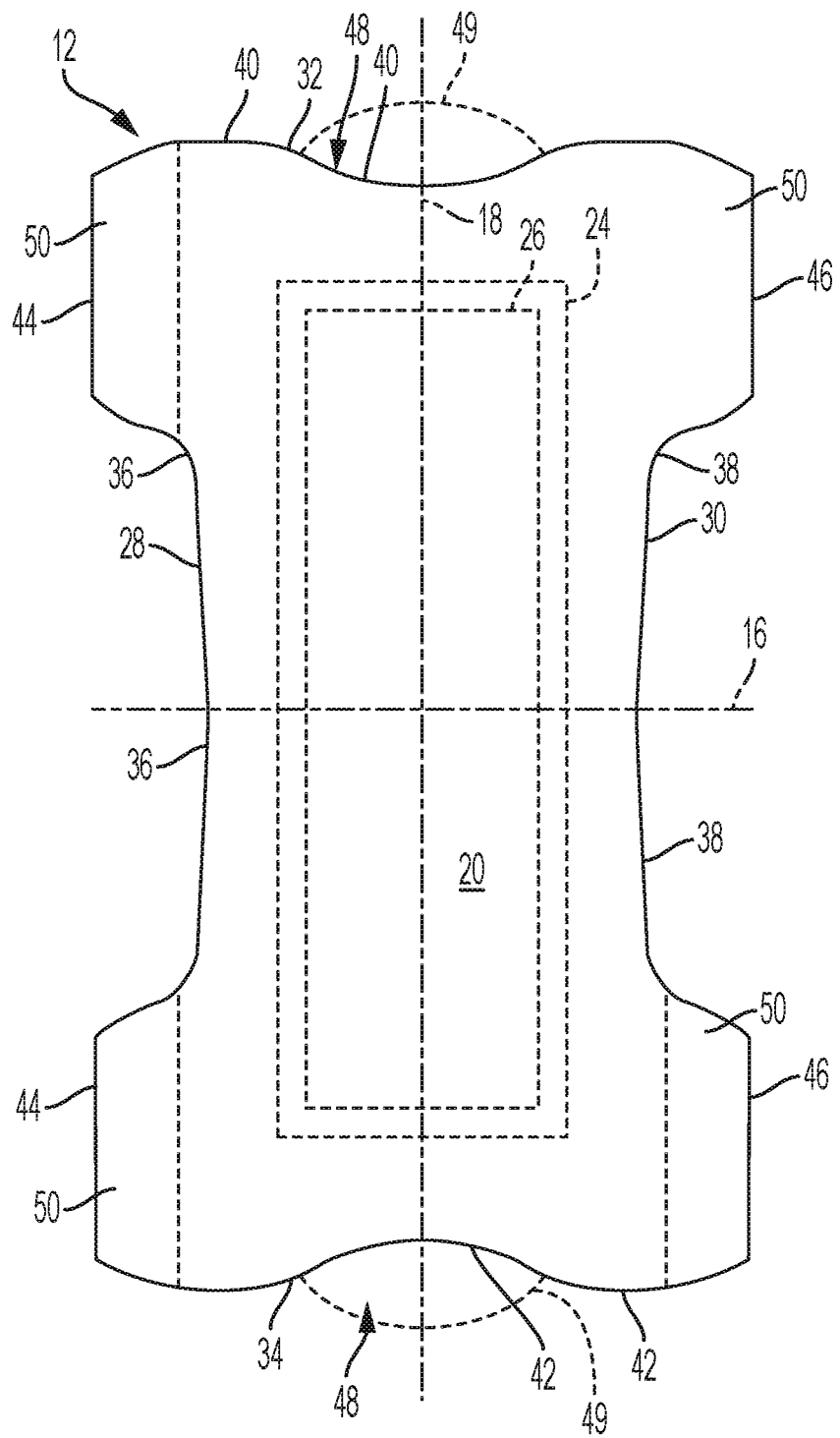
FIG. 4 is a plan view of an absorbent article chassis of the present disclosure, wearer-facing surface facing the viewer, and without the removable fastening members attached thereto.

The absorbent articles of the present disclosure may have waist and/or side edges each having one or more curvilinear or arcuate portions. This enables the absorbent articles to better fit smaller infants or other wearers, due to their curvilinear surfaces. The curvilinear portions also aid in the consumer perception of softness and intentionality/customization of the absorbent articles. FIG. 1 is a front perspective view photograph of an absorbent article of the present disclosure in an in-use configuration. FIG. 2 is a side view photograph of the absorbent article of FIG. 1 in the in-use configuration. FIG. 3 is a plan view of an absorbent article of the present disclosure, garment-facing surface facing the viewer, and with removable fastening members attached to an outer cover nonwoven material. FIG. 4 is a plan view of an absorbent article chassis of the present disclosure, wearer-facing surface facing the viewer, and without the removable fastening members attached thereto.

Referring to FIGS. 3 and 4, an absorbent article 10 of the present disclosure may comprise a chassis 12 and one or more, such as two, fully removable fastening members 14. The removable fastening members will be discussed in further detail below. The chassis 12 may comprise a central lateral axis 16 and a central longitudinal axis 18. The chassis 12 may comprise a first waist region 11, a second waist region 13, and a crotch region 15 extending intermediate the first waist region and the second waist region. The chassis 12 may comprise a liquid permeable topsheet 20 (FIG. 4) forming a portion of a wearer-facing surface of the chassis 12, a liquid impermeable backsheet 21, an outer cover nonwoven material 22 forming a portion of a garment-facing surface of the chassis 12, and an absorbent core 24. The absorbent core 24 may comprise a core wrap and may have a first outer surface configured to face toward a wearer-facing surface in an absorbent article and a second outer surface configured to face toward a garment-facing surface in an absorbent article. The topsheet may be apertured or non-apertured and may or may not comprise three-dimensional elements, patterns, and/or embossing. The backsheet 21 may comprise a breathable or a non-breathable film. The outer cover nonwoven material 22 may or may not comprise apertures, three-dimensional elements, patterns, and/or embossing. The chassis 12 may comprise an acquisition material 26 positioned at least partially intermediate the topsheet 20 and the absorbent core 24. The chassis 12 may comprise a first side edge 28, a second side edge 30, a first waist edge 32, and a second waist edge 34. The first side edge 28 may be positioned on a first side of the central longitudinal axis 18 with the second side edge 30 positioned on a second side of the central longitudinal axis. The first waist edge 32 may be positioned on a first side of the central lateral axis 16 with the second waist edge 34 positioned on a second side of the central longitudinal axis. The first side edge 28 may comprise one or more first curvilinear portions 36. The second side edge 30 may comprise one or more second curvilinear portions 38. The first waist edge 32 may comprise one or more first curvilinear portions 40. The second waist edge 34 may comprise one or more second curvilinear portions 42. The first side edge 28 may comprise one or more linear portions 44. The second side edge 30 may comprise one or more linear portions 46. The first and second waist edges 32, 34 may each comprise one or more linear portions or may not comprise any linear portions.

The chassis 12 may be substantially symmetrical about the central lateral axis 16 and/or may be substantially symmetrical about the central longitudinal axis 18 to provide reversibility. Likewise, the first side edge 28 may be substantially symmetrical to the second side edge 30 about the central longitudinal axis 18 and the first waist edge 32 may be substantially symmetrical to the second waist edge 34 about the central lateral axis 16 again to provide reversibility. "Substantially symmetrical" means planned to be symmetrical, but allowing for manufacturing tolerances. In addition to the side and/or waist edges, the absorbent core 24, the optional acquisition material 26, the backsheet 21, the outer cover nonwoven material 22 (or other materials, such as a distribution layer) may be substantially symmetrical about the central lateral axis 16 and/or the central longitudinal axis 18. By having the chassis 12 and its components be substantially symmetrical about the central lateral and longitudinal axes 16, 18, the absorbent article may be fully reversible, thereby allowing a caregiver or nurse the ability to apply the absorbent article with either of the first or second waist edge on a front waist of a wearer. This reversibility is especially helpful in the context of premature infants as they may be positioned in various positions and it is desired to move them as little as possible. In some instances, the chassis 12 may not be substantially symmetrical about the central lateral axis 16 and/or the central longitudinal axis 18. In this instance, the chassis 12 may or may not still be reversible.

Referring again to FIGS. 3 and 4, the first curvilinear portion 40 of the first waist edge 32 may comprise one or more first concave portions and one or more first convex portions with respect to the central lateral axis 16. Likewise, the second curvilinear portion 42 of the second waist edge 34 may comprise one or more first concave portions and one or more first convex portions. In some instances, the entire first and second waist edges 32, 34 may have a single concave portion and two convex portions with respect to the central lateral axis 16. The concave portions of the first and second waist edges, or portions thereof, may form umbilical cord or surgical site notches or recesses 48 in the first and second waist edges. The gradual slopes into the umbilical cord or surgical site notches or recesses 48 may be important in a premature baby context. These gradual slopes may allow nurses to easily adjust the absorbent article (i.e., pull toward the front or back) depending on the size of the infant and/or the location of a surgical site or belly button. Instead of umbilical cord or surgical site notches or recesses, the chassis 12 may have umbilical cord or surgical site projections (shown in dash) to cover the belly button or surgical site.

Figure 3A:
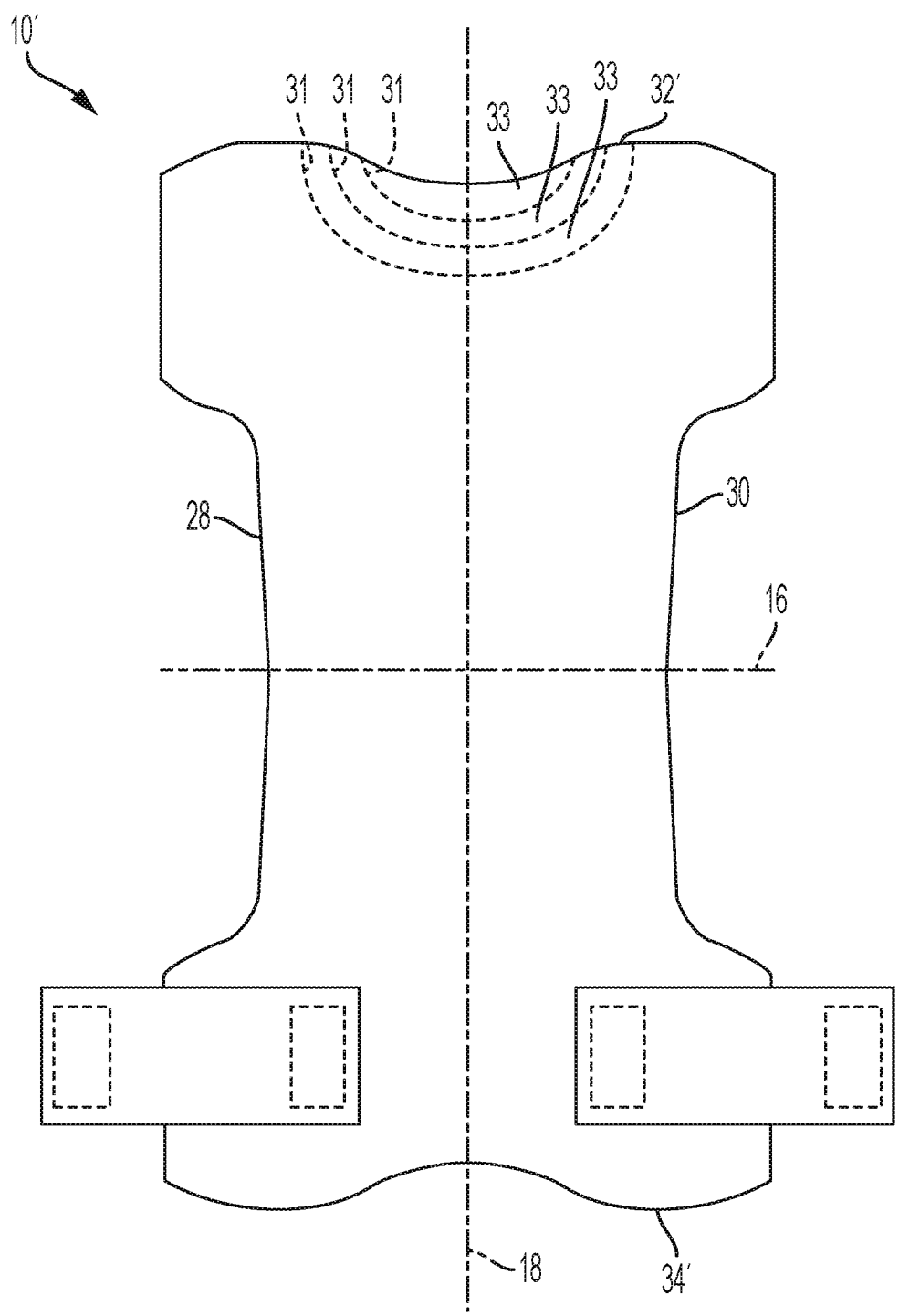
FIG. 3A is a plan view of an absorbent article of the present disclosure comprising one or more lines of perforations.
Figure 3B:
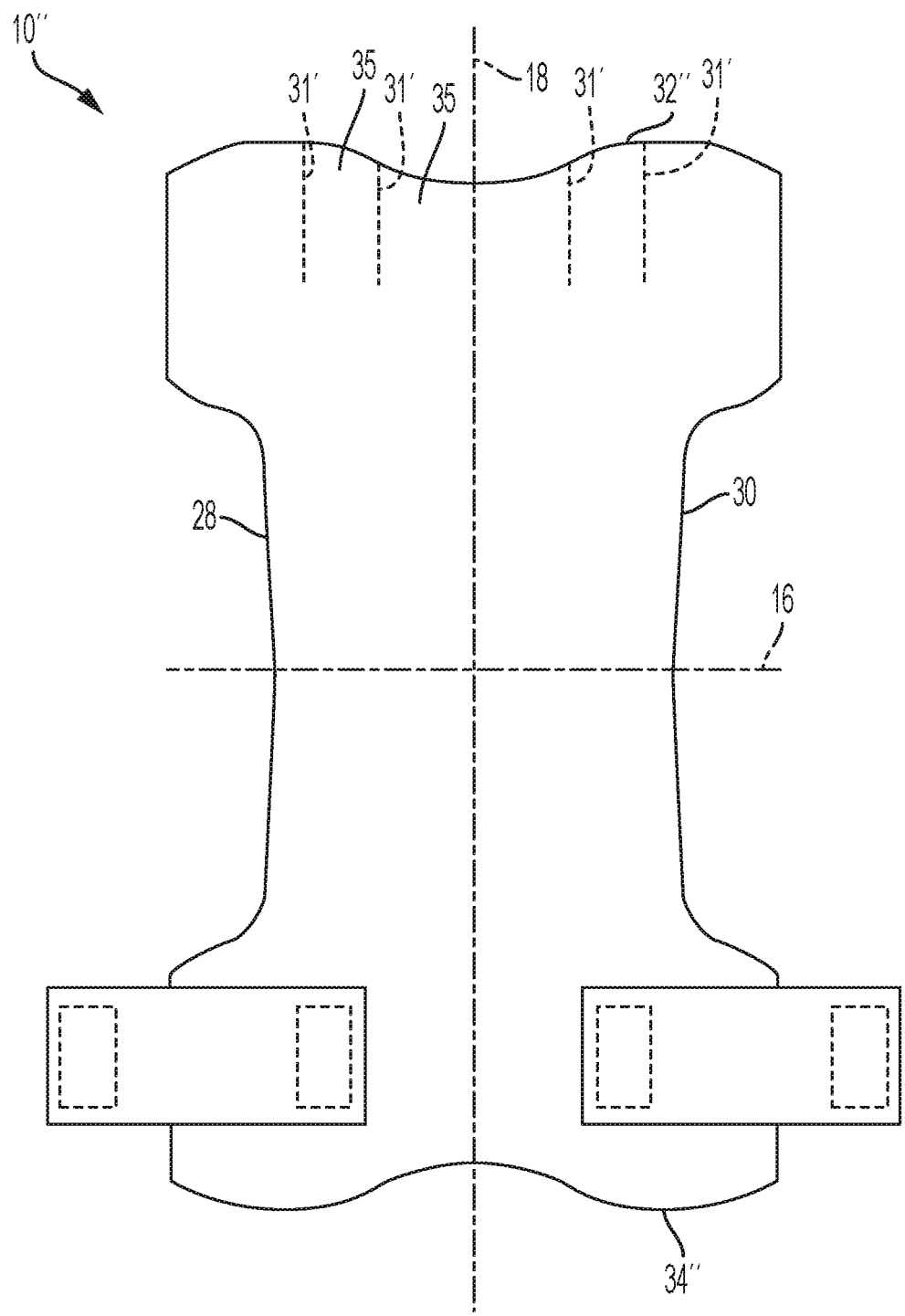
FIG. 3B is a plan view of an absorbent article of the present disclosure comprising one or more lines of perforations.

In some instances, the first waist edge and/or the second waist edge of an absorbent article may be provided with optional umbilical cord notches or foldable areas so that a nurse may decide whether to remove/fold over a portion of the absorbent article or not depending on the diapering situation he or she may be encountering. Referring to FIG. 3A, an absorbent article 10' may comprise one or more lines of perforations 31 proximate to a first waist edge 32' and/or a second waist edge 34'. The lines of perforations 31 may extend through the thickness of the absorbent article 10' so that a nurse may tear along one of the lines of perforations 31 to create an umbilical cord notch of varying desired size. A removable area 33 of the chassis is positioned intermediate the lines of perforations 31 and the first waist edge 32'. The removable area 33 may comprise one or more of the lines of perforations 31 depending on which line of perforations 31 the nurse chooses to tear. The lines of perforations 31 may also be provided proximate to the second waist edge 34'. The lines of perforations 31 may comprise arcuate or curvilinear portions. Referring to FIG. 3B, an absorbent article 10" may comprise two or more lines of perforations 31" proximate to the first waist edge 32" or the second waist edge 34". The lines of perforations 31" may extend through the thickness of the absorbent article 10" so that a nurse may tear along two of the lines of perforations 31" to create an umbilical cord notch of varying desired size (in both the lateral direction and the longitudinal direction). This tearing along the two lines of perforation 31" leaves behind a foldable area 35 of the chassis between the first and second lines of perforation 31". The foldable area 35 of the chassis may comprise one or more lines of perforations 31" depending on what two lines of perforations 31" the nurse tears. In such a configuration, the nurse may fold at least a portion of the foldable area 35 over the wearer-facing surface or the garment-facing surface of the absorbent article to create the umbilical cord notch. The nurse may optionally tape or otherwise attach a portion of the foldable area 35 to the wearer-facing surface or to the garment-facing surface or cut away the material with scissors, for example. The lines of perforations 31" may also be provided proximate to the second waist edge 34".

The chassis 12 may be a uni-body chassis or may have protrusions 50 (shown with dashes) attached thereto. The protrusions 50 may be attached to a main body of chassis (i.e., chassis 12 without the protrusions 50) much like ears are attached to commercially available absorbent articles, such as through the use of adhesives and/or bonding. In a non-uni-body configuration, first and second protrusions 50 may be attached proximate to the first side edge 28 and third and fourth protrusions 50 may be attached proximate to the second side edge 30. In a uni-body configuration, a first protrusion 50 may be formed in the first side edge 28, a second protrusion may be formed in the second side edge 30, a third protrusion may be formed in the first side edge, and a fourth protrusion may be formed in the second side edge 30. Each of the first, second, third, and fourth protrusions, in the uni-body configuration, are not separate elements from the chassis 12. In either configuration, at least one of, two of, three of, or all of the protrusions 50 may each have one or more additional curvilinear portions (separate from curvilinear portions in the side edges). A uni-body configuration may be desired because the absorbent article would not have seams (where components are joined to each other), thereby leading to improved softness and improved leakage protection.

The first and second side edges 28, 30 and the first and second waist edges 32, 34 may together form an outer perimeter of the chassis 12. In the context of the uni-body chassis and the non-uni-body chassis, the projections 50 form portions of the first and second side edges and, thereby, the outer perimeter. About 40% to about 95%, about 50% to about 95%, about 60% to about 95%, or about 60% to about 90%, of the outer perimeter may be curvilinear, specifically reciting all 1% increments within the specified ranges and all ranges formed therein or thereby. Only about 5% to about 50%, about 5% to about 40%, about 5% to about 30%, or about 5% to about 25%, of the outer perimeter may be linear (i.e., straight), specifically reciting all 1% increments within the specified ranges and all ranges formed therein or thereby.

On an absorbent article manufacturing line, a web having an infinite length is typically conveyed in a machine direction. These webs typically have linear side edges and are cut in a cross-machine direction to an absorbent article pitch. The one or more linear portions 44 and the one or more linear portions 46 may be portions of the linear side edges of the webs, while the curvilinear portions 36, 38, 40, 42 may be formed by additional cutting and removal of the cut portions (i.e., trim removal).

Figure 5:
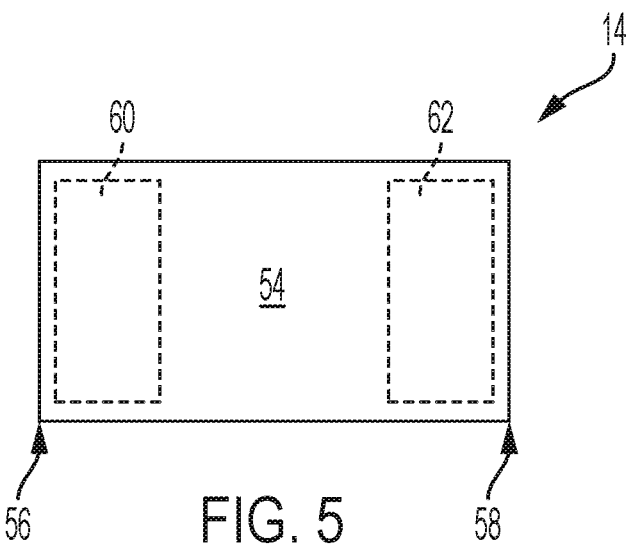
FIG. 5 is a plan view of a second surface of a removable fastening member.
Figure 6:
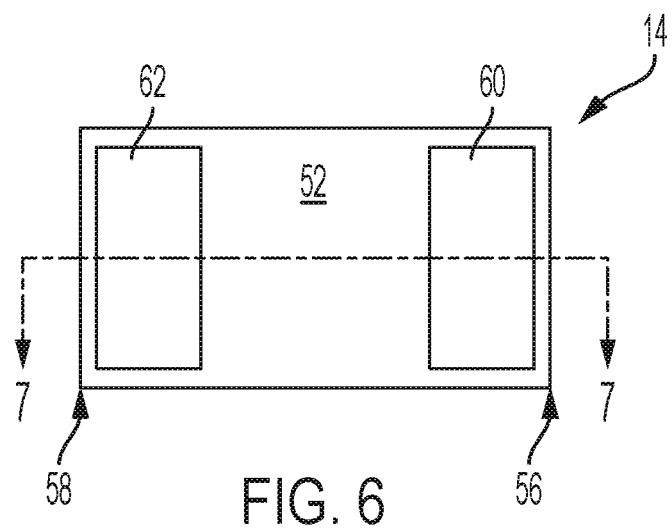
FIG. 6 is a plan view of a first surface of the removable fastening member of FIG. 5.
Figure 7:
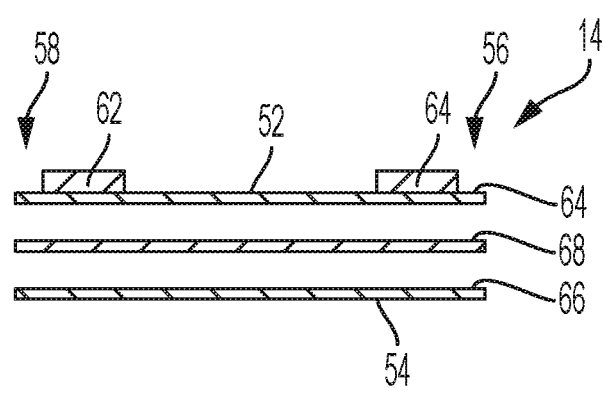
FIG. 7 is a cross-sectional view of the removable fastening member taken about line 7-7 of FIG. 6.

FIG. 5 is a plan view of a second surface of a removable fastening member. FIG. 6 is a plan view of a first surface of the removable fastening member of FIG. 5. FIG. 7 is a cross-sectional view of the removable fastening member taken about line 7-7 of FIG. 6. The fully removable fastening members 14 may be stretch panels that may be discrete elements from the chassis 12. Referring to FIGS. 5 and 6, the fastening members 14 may each comprise a first surface 52, a second surface 54, a first end 56, and a second end 58. The first surface 52 may be opposite to the second surface 54 and the first end 56 may be opposite to the second end 58. The fastening members 14 may comprise a first fastener 60 that may be configured to engage a first portion of the outer cover nonwoven material 22 or a first portion of a landing zone (if provided) and be positioned on the first surface 52. The first fastener 60 may be configured to engage a portion of the chassis 12 on a first side of the central lateral axis 16. The chassis 12 may be free of a landing zone and any portion of the outer cover nonwoven material 22 may function as the landing zone. The fastening members 14 may comprise a second fastener 62 that may be configured to engage a second, different portion of the outer cover nonwoven material 22 and positioned on the first surface 52. The second fastener 62 may be configured to engage a portion of the chassis 12 on a second side of the central lateral axis 16. In some instances, only one fully removable fastening member 14 may be provided with a chassis 12. In this scenario, the first fastener 60 may engage a portion of the outer cover nonwoven material 22 of the chassis 12 and the second fastener 62 may engage another portion of the outer cover nonwoven material 22 or may engage a portion of the second surface 54 of the fastening member 14. The fastening members 14 may be provided in a package with one of the fasteners 60, 62 attached to portions of the outer cover nonwoven material and with the other fastener 60, 62 engaged with the topsheet 20 (or other portion of the chassis) or not engaged to any portion of the chassis 12. The other fastener 60, 62 may also be engaged with a surface 52, 54 of the fastening members to at least inhibit the fasteners 60, 62 from catching on other absorbent articles or other items. In still other instances, the fastening members 14 may be provided in a package with the chassis 12, but be separate from the chassis 12. In other instances, the fastening member 14 and the chassis 12 may be provided in separate packages.

Since the fastening members 14 are fully removable from the absorbent article 10, they can be fastened as desired by a nurse or caregiver. In some instances, the nurse or caregiver may remove the fastening members 14 from the chassis 12 and not use them if the infant is in a certain position, for example. In other instances, the nurse or caregiver may only use one of the fastening members 14 if the infant is in another certain position, for example.

Referring to FIGS. 5 and 6, the first fastener 60 and the second fastener 62 may not extend to the outer perimeter of the fastening members 14. This may help prevent, or at least inhibit, rough fastener material (e.g., hooks) from contacting or irritating a wearer's skin. The fasteners 60 and 62 are illustrated as rectangular but may be any other suitable shape, such as circular or ovate, for example. In some instances, it may be desirable to have fasteners without corners to again prevent, or at least inhibit the fasteners from irritating a wearer's skin.

Referring to FIG. 7, the fastening members 14 may comprise a first nonwoven or other substrate 64, a second nonwoven or other substrate 66, and an elastic material 68 positioned at least partially intermediate the first and second substrates 64 and 66. The elastic material 68 may comprise an elastic nonwoven material, an elastic film, and/or elastic strands, for example. The elastic material may be apertured or micro-apertured to promote breathability. In other instances, the fastening members may comprise one or more substrates and may not comprise an elastic material. In still other instances the fastening member may comprise one or more elastic nonwoven substrates.

Figure 8:
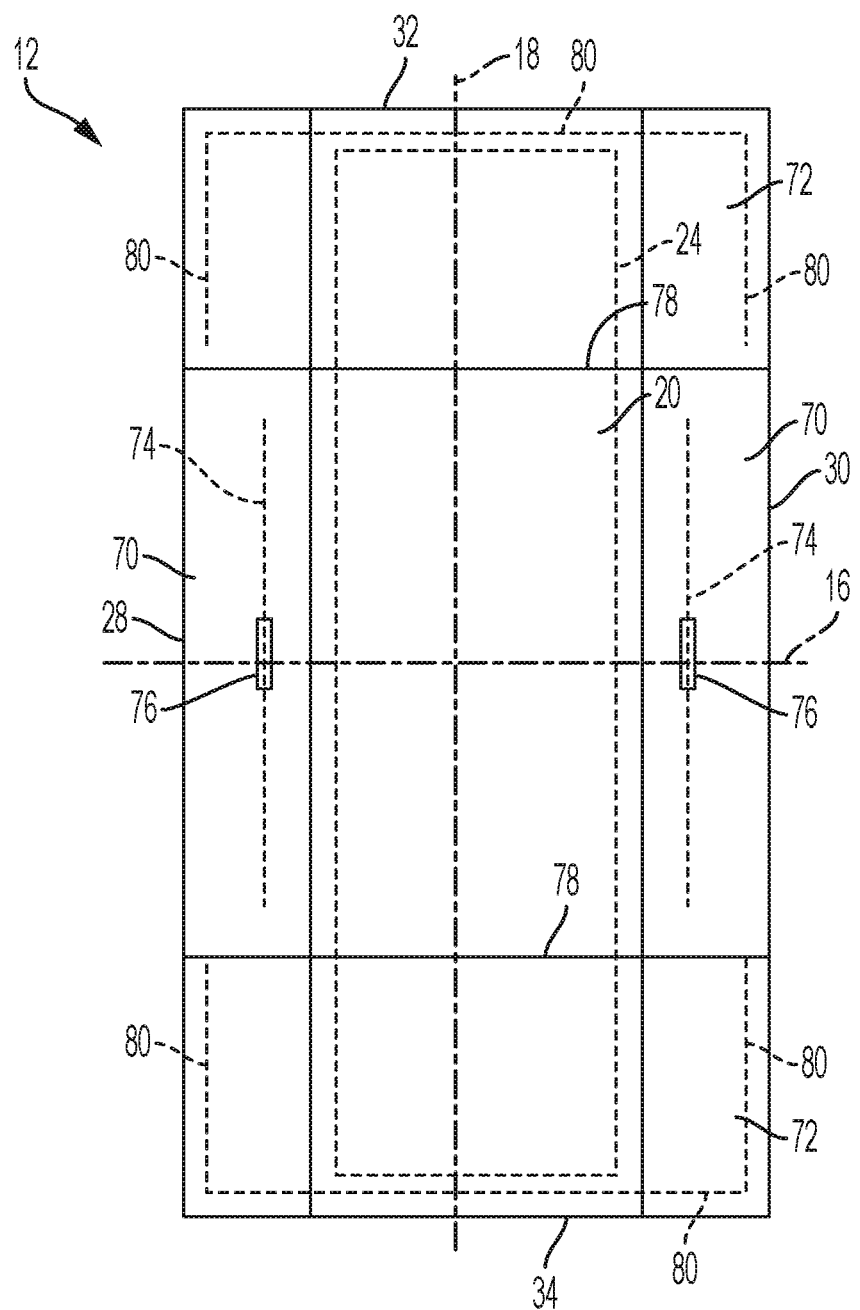
FIG. 8 is a plan view of an example absorbent article chassis of the present disclosure with wetness guards and leg cuffs, wearer-facing surface facing the viewer.

FIG. 8 is a plan view of an example absorbent article chassis 12 of the present disclosure with wetness guards and leg cuffs, wearer-facing surface facing the viewer. The fully removable fastening members 14 may be used with the absorbent article chassis 12, much like illustrated in FIG. 3 and discussed herein. The example absorbent article chassis 12 is not illustrated with the curvilinear portions on the waist and side edges 32, 34, 28, 30 for simplicity in illustration, although it will be understood that the chassis may have the same or similar shape as the chassis of FIGS. 3 and 4. The absorbent article chassis 12 may comprise one or more pairs of leg cuffs 70 and one or more wetness guards 72. The leg cuffs 70 may have one or more elastic strands 74 positioned therein. The elastic stands 74 may be attached to the cuffs only in a central zone 76 proximate to the central lateral axis 16. As an example, the central zone 76 may extend between about 0.5 inches and about 2.5 inches in a smaller sized absorbent article. In the central zone 76, the elastic strand 74 may be glued or bonded to a portion of the leg cuff. In some instances, only one pair of leg cuffs may be provided. Additional features of the leg cuffs are disclosed in U.S. Patent Application Publication No. 2017/0246052, to Ludwig et al., published on Aug. 31, 2017.

One or more wetness guards 72 may be provided on a wearer-facing surface of the chassis 12. In some instances, only one wetness guard may be provided on a longitudinally end region of the chassis 12. In other instances, two wetness guards may be provided on longitudinally opposite end regions of the chassis 12. When bodily exudates, especially urine, enter an absorbent article they may initially be absorbed in a central longitudinal region of the absorbent article or the crotch region. By design, and to inhibit the crotch region from becoming overloaded, the bodily exudates are wicked towards longitudinal end region of the absorbent article by the acquisition material and the absorbent core. This allows the crotch region to be able to accept additional insults of bodily exudates without overloading. This also potentially makes the longitudinal end regions wet. In order to protect an infant's skin in contact with the longitudinally end regions, such as the lower back and the front waist of a wearer, wetness guards may be provided in one or both of the longitudinally end regions. The wetness guards 72 may each overlap a portion of the topsheet 20 to inhibit topsheet to skin contact and thereby reduce moisture on the skin of a wearer.

The wetness guards 72 may comprise one or more layers of material. In an instance, the wetness guards may comprise a film facing the topsheet 20 and one or more nonwoven materials facing the wearer. In other instances, the wetness guards 72 may comprise a hydrophobic nonwoven material without a film. By providing a film or a hydrophobic nonwoven material, wetness from the absorbent core or acquisition material may be shielded from contacting the lower back or the front waist of a wearer, thereby improving skin health and dryness.

Figure 9:
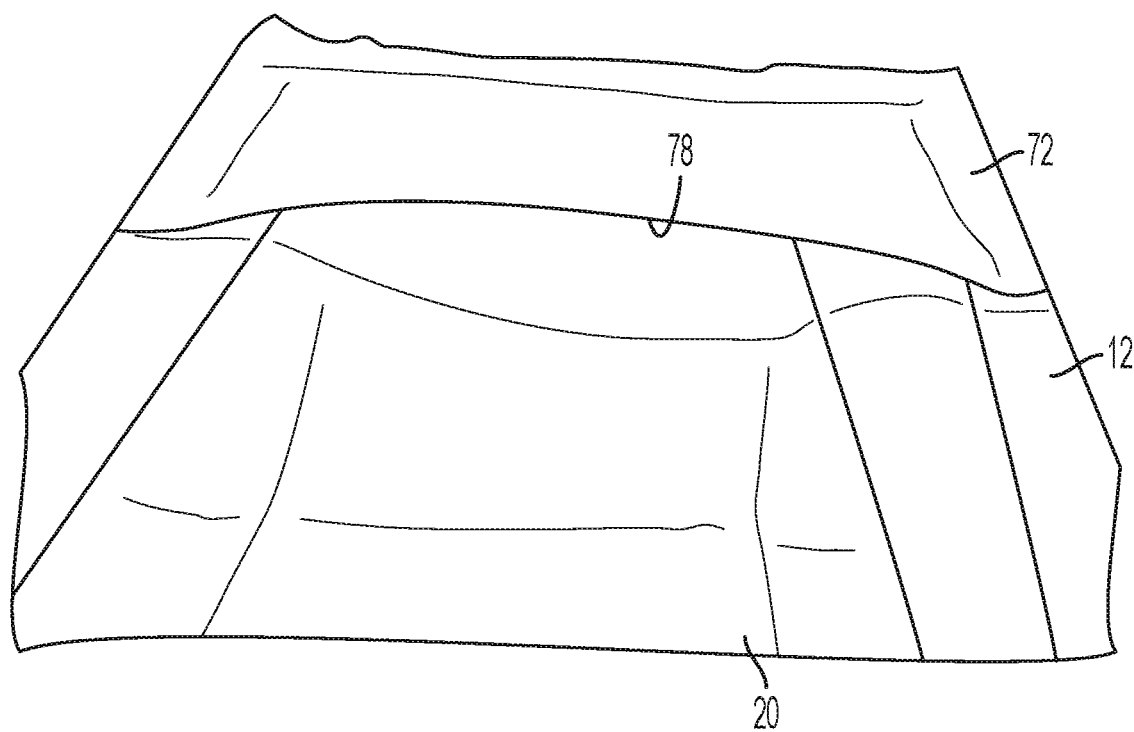
FIG. 9 is a photograph of an example wetness guard of the present disclosure, wearer-facing surface facing the viewer.

In some instances, the wetness guards 72 may be formed of portions of the backsheet film 21 and outer cover nonwoven 22 folded over the waist edges 32, 34. In other instances, the wetness guards may be discrete components attached to the chassis 12. FIG. 9 illustrates a photograph of a wetness guard 72 attached to a chassis 12, wearer-facing surface facing the viewer. The wetness guards 72 may have a free, unattached end 78 most proximate to the central lateral axis 16. The free, unattached end 78 is illustrated as linear in FIG. 9, but may comprise curvilinear portions. The wetness guards may be fully removable from the chassis 12, if desired, by providing hooks or other attachment features on the topsheet facing side of the wetness guards and/or on the topsheet. In other instances, the wetness guards 72 may be permanently bonded, adhesively attached, or otherwise attached, to the chassis 12, for example along attachment area 80. Additional features of the wetness guards are disclosed in U.S. Patent Application Publication No. 2017/0246052, to Ludwig et al., published on Aug. 31, 2017.

Absorbent Article Dimensions

The absorbent articles of the present disclosure may have an absorbent article length along the central lateral axis 18 (see FIG. 3) of about 50 mm to about 500 mm, about 100 mm to about 400 mm, about 100 mm to about 300 mm, about 150 mm to about 200 mm, about 150 mm to about 250 mm, or about 200 mm to about 250 mm, specifically reciting all 0.1 mm increments within the specified ranges and all ranges formed therein or thereby. Other absorbent article lengths are also within the scope of the present disclosure.

The absorbent articles of the present disclosure may have an absorbent article width along the central lateral axis 16 (see FIG. 3) in the range of about 25 mm to about 300 mm, about 25 mm to about 200 mm, about 50 mm to about 150 mm, or about 50 mm to about 100 mm, specifically reciting all 0.1 mm increments within the specified ranges and all ranges formed therein or thereby. Other absorbent article widths are also within the scope of the present disclosure.

The absorbent articles of the present disclosure may have an absorbent article area in the range of about 100 $cm^2$ to about 500 $cm^2$, about 125 $cm^2$ to about 400 $cm^2$, about 150 $cm^2$ to about 350 $cm^2$, about 150 $cm^2$ to about 325 $cm^2$, about 150 $cm^2$ to about 175 $cm^2$, or about 275 $cm^2$ to about 300 $cm^2$, specifically reciting all 0.1 $cm^2$ increments within the specified ranges and all ranges formed therein or thereby. Other absorbent article areas are also within the scope of the present disclosure.

Fully Removable Fastening Members

Figure 10:
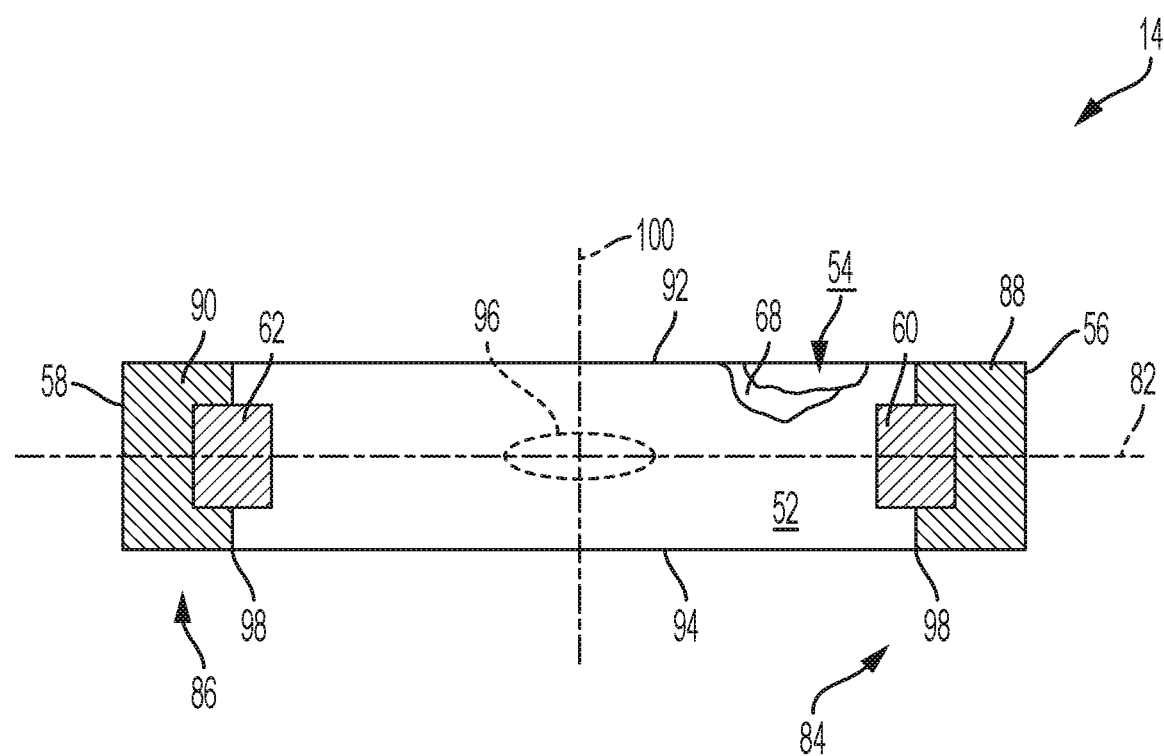
FIG. 10 is a plan view of a removable fastening member comprising fasteners and grasp regions.

Some details of the fully removable fastening members 14 of the present disclosure are discussed above. Those details apply to the fully removable fastening members 14 discussed below as well. FIG. 10 illustrates an example fully removable fastening member 14 of the present disclosure. Referring to FIGS. 3 and 10, the fully removable fastening member 14 is configured to join a portion of the first waist region 11 of the absorbent article 10 to the second waist region 13 of the absorbent article 10. In some instances, two fastening members 14 may be provided for a certain absorbent article. Each fastening member 14 may have a central lateral axis 82, a central longitudinal axis 100, a first nonwoven material comprising a first surface 52, a second nonwoven material comprising a second surface 54 opposite to the first surface 52, and an optional elastic material 68 positioned intermediate the first and second nonwoven materials. The elastic material 68 may comprise elastic strands or an elastic film. Each of the fastening members 14 may comprise a first end region 84 comprising the first end 56 and a second end region 86 comprising the second end 58. The first end region 84 is positioned opposite to the second end region 86. The first end region 84 may or may not be substantially symmetrical to the second end region 86. The fastening member 14 may or may not be substantially symmetrical about the central longitudinal axis. The fastening members 14 may comprise a first fastener 60 on the first surface 52 and positioned in the first end region 84 and a second fastener 62 on the first surface 52 and positioned in the second end region 86.

Again, referring to FIG. 10, the fastening members 14 may comprise a first grasp region 88 either partially laterally outboard of the first fastener 60 or fully laterally outboard of the first fastener 60 in the first end region 84 and proximate to the first end 56. The first grasp region 88 may also be fully overlapped by the first fastener 60 such that the first grasp region 88 extends laterally outboard of the first fastener 60 and laterally inboard of the first fastener 60. In some instances, it may be desirable to only have one grasp region on a fastening member 14. In other instances, it may be desirable to have two grasp regions on a fastening member 14. In such an instance, the fastening members 14 may comprise a second grasp region 90, either partially laterally outboard of the second fastener 62 or fully laterally outboard of the second fastener 62, in the second end region 86 and proximate to the second end 58. The second grasp region 90 may also be fully overlapped by the second fastener 62 such that the second grasp region 90 extends laterally outboard of the second fastener 62 and laterally inboard of the second fastener 62. The various grasp regions may have a different physical property than a remainder of the fully removable fastening member in areas free of the fasteners. The physical property may be thickness, basis weight, texture, three-dimensionality, coefficient of friction, stiffness, and/or number of materials. The fasteners 60, 62 may overlap, or overlap a portion of, a seam or line of discontinuity 98. The seam or line of discontinuity may comprise a fold line in the nonwoven materials or elastic materials, an adhesive strip, an overlap of two or more materials, a color contrast (e.g., blue on one side and green on the other side, or dark blue on one side and light blue on the other side), a deposited material, an indented or perforated region, a ruptured region, a melted region, a texture difference, a stiffness difference, and/or a basis weight difference, for example. The benefit of the seam or line of discontinuity may be at least two-fold. First, the seam or line of discontinuity may provide a visual or tactile signal or assurance of the correct place to grasp the fastening members. Second, the seam or line of discontinuity may provide additional grasp strength and/or security via a physical advantage (3-dimensionality and/or friction) to aid the caregiver in applying, readjusting, and/or removing the fastener.

Referring still to FIG. 10, the first and second fasteners 60, 62 on each fastening member 14 may each comprise a plurality of hooks, loops, or other attachment mechanisms. The fastening member 14 may comprise a first side edge 92 and a second side edge 94. The first fastener 60 may be spaced apart from the first side edge 92, the second side edge 94, and the first end 56. The second fastener 62 may be spaced apart from the first side edge 92, the second side edge 94, and the second end 58. Providing spacing between a perimeter of the fastening member 14 and the fasteners 60, 62, helps avoid hooks or corners of the fasteners from contacting the skin of a wearer.

Any of the fastening members 14 may comprise one or more apertures or slots 96 therein intermediate the first end 56 and the second end 58 or intermediate the first and second fasteners 60, 62. The apertures or slots 96 may be useful in receiving medical tubes, thermometers etc. therethrough in a neonatal or other setting.

As illustrated in FIG. 3, two fastening members may be provided with a single chassis 12. The second fastening member may have the same features as explained herein with regard to the fastening member 14, including the grasp regions and other features. As shown in FIG. 3, the fastener 62 may be removably attached to the outer cover nonwoven material 22 in the second waist region 13 when the absorbent article 10 comes to a nurse or caregiver. In other instances, the fastener 62 may be removably attached to the outer cover nonwoven material 22 in the first waist region 11 when the absorbent article 10 comes to a nurse or caregiver. The other fastener 60 may be attached to a wearer-facing side of the chassis 12, for example. The fastener 62 that is attached to the outer cover nonwoven material 22 may have a higher fastening force than the fastener 60. This may be helpful in that even though both of the fasteners are removable, a nurse or caregiver may choose to leave the fastener 62 attached to the outer cover nonwoven material 22 as presented to the consumer and merely attach the fastener 60 to the outer cover nonwoven material when donning the absorbent article.

Figure 11:
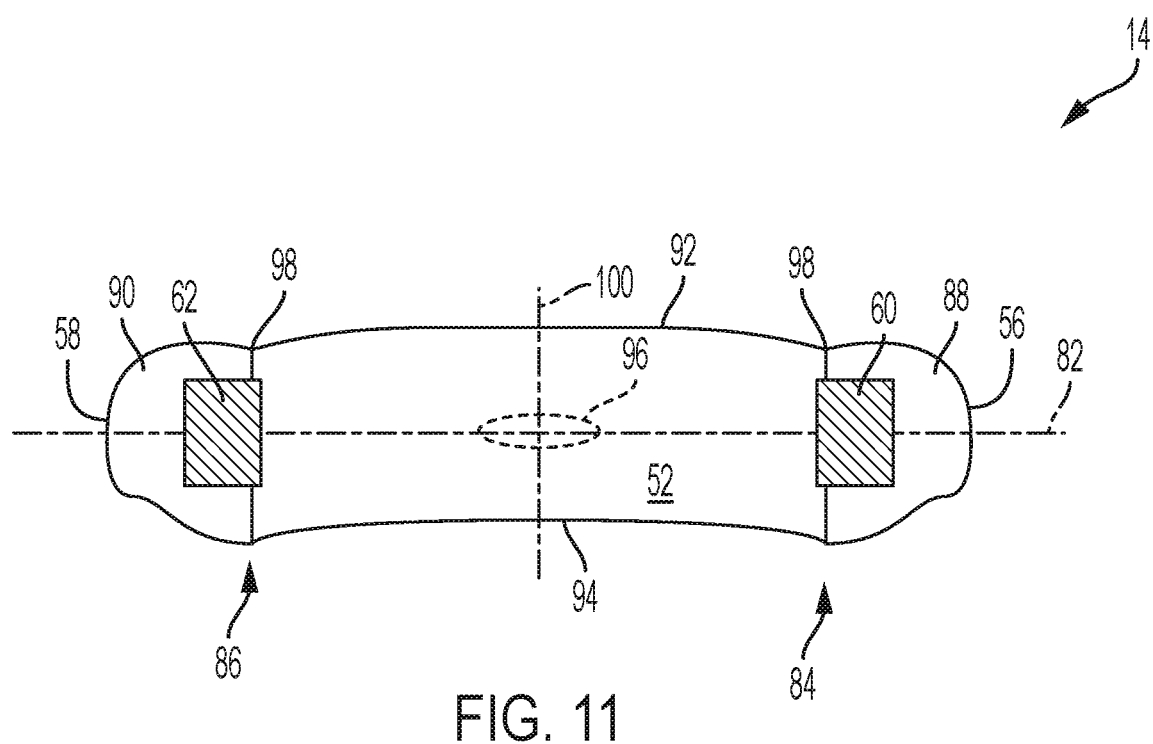
FIG. 11 is a plan view of a removable fastening member comprising fasteners and grasp regions and comprising curvilinear portions.

FIG. 11 is another example shape of a fastening member 14 with first and second grasp regions 88, 90 and first and second fasteners 60, 62. Like numbers to the fastening member 14 of FIG. 10 indicate like elements in FIG. 11. The first and second side edges 92, 94, or portions thereof, may comprise one or more curvilinear portions. The first and second side edges 92, 94, or portions thereof, may be substantially symmetrical or asymmetrical about the central lateral axis 82. In some instances, the first and second side edges 92, 94 may comprise one or more concave or convex portions relative to the central lateral axis 82. As an example, the first side edge 92 may comprise a convex portion and the second side edge 94 may comprise a concave portion both relative to the central lateral axis 82. The first grasp region 88 and the second grasp region 90 may comprise at least one, two, three, or four curvilinear portions, for example. The first grasp region 88 and the second grasp region 90 may comprise at least one concave portion and at least one convex portion relative to the central lateral axis 82 or the central longitudinal axis 100 perpendicular to the central lateral axis 82. The first grasp region 88 may or may not be substantially symmetrical to the second grasp region 90. The curvilinear portions or concave and convex portions of the fastening member 14 of FIG. 11 aid in fitting wearers of many different shapes and sizes and better fit the curved features of a baby. Only one of the grasp regions may be provided on the fastening member 14 of FIG. 11. The first and second grasp regions may have a different physical property than a remainder of the fully removable fastening member in an area not overlapping the fasteners. The physical property may be thickness, basis weight, texture, three-dimensionality, coefficient of friction, stiffness, number of materials, and/or other physical properties discussed herein. The fastening member 14 of FIG. 11 may be substantially symmetrical about the central longitudinal axis 100.

Figure 12:
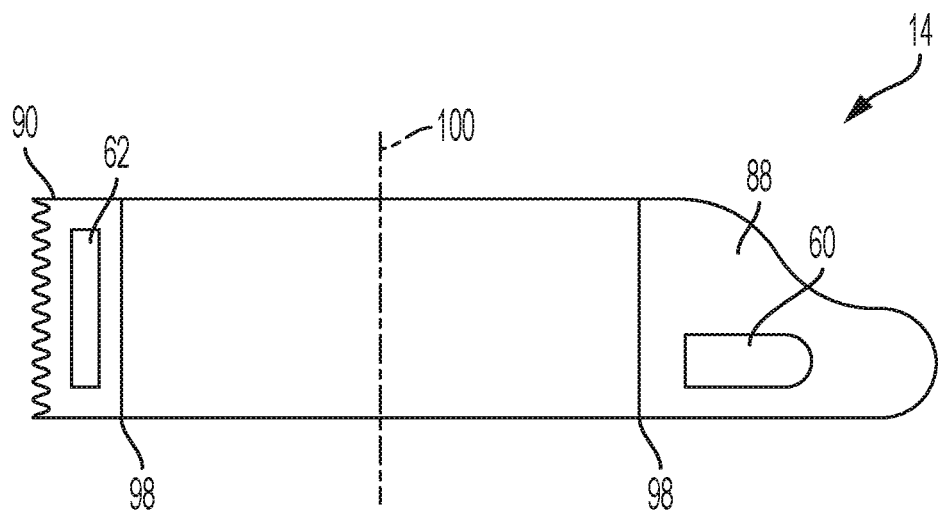
FIG. 12 is a plan view of a removable fastening member comprising fasteners and grasp regions comprising curvilinear portions.
Figure 13:
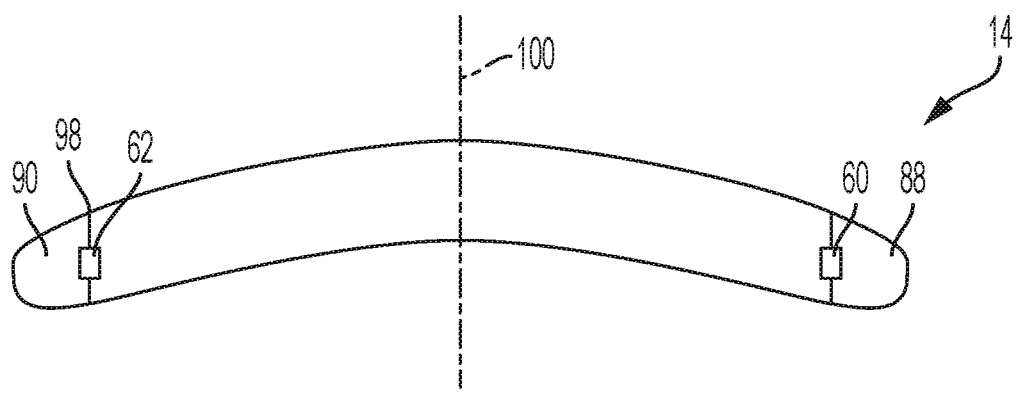
FIG. 13 is a plan view of a removable fastening member comprising fasteners and grasp regions and comprising curvilinear portions.

FIG. 12 is an example of a fastening member 14 that is asymmetrical about the central longitudinal axis 100. It is noted that the first and second fastening members 60, 62 may have different sizes, shapes, and/or orientations as well. At times, the size, shape, and/or orientation may match or be configured to coordinate with the shape, size, and/or orientation of the first and second grasp regions 88, 90. The first and second grasp regions may have a different physical property than a remainder of the fully removable fastening member in areas not comprising the fasteners. The physical property may be thickness, basis weight, texture, three-dimensionality, coefficient of friction, stiffness, number of materials, and/or other physical properties discussed herein. Only one of the grasp regions may be provided on the fastening member 14 of FIG. 12. In this example, the first and second fasteners may not overlap a seam or line of discontinuity. FIG. 13 is another example of a shape of fastening member 14 that is substantially symmetrical about the central longitudinal axis 100.

Figure 14:
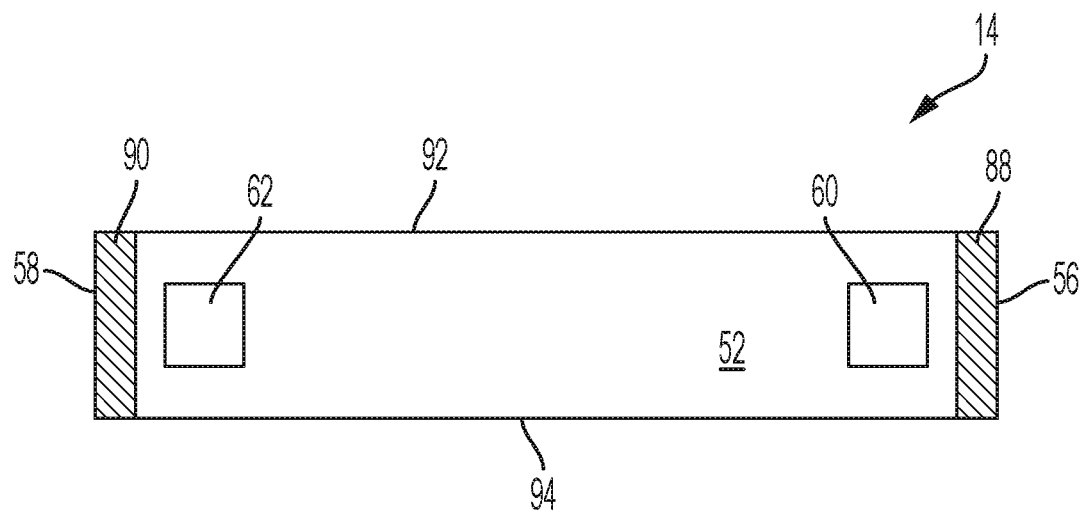
FIGS. 14-17 are plan views of one side of removable fastening members comprising fasteners and grasp regions, showing different locations and configurations of the grasp regions.
Figure 15:
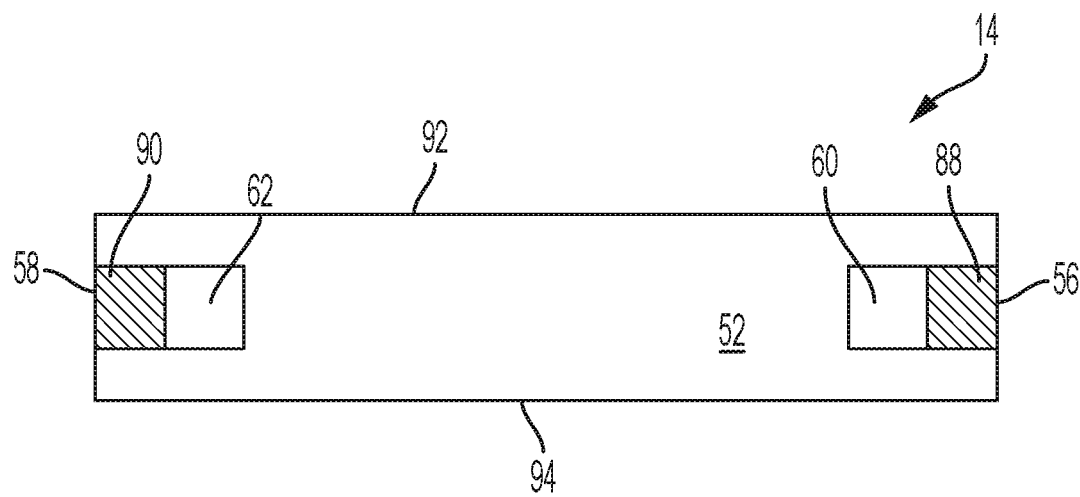
Figure 16:
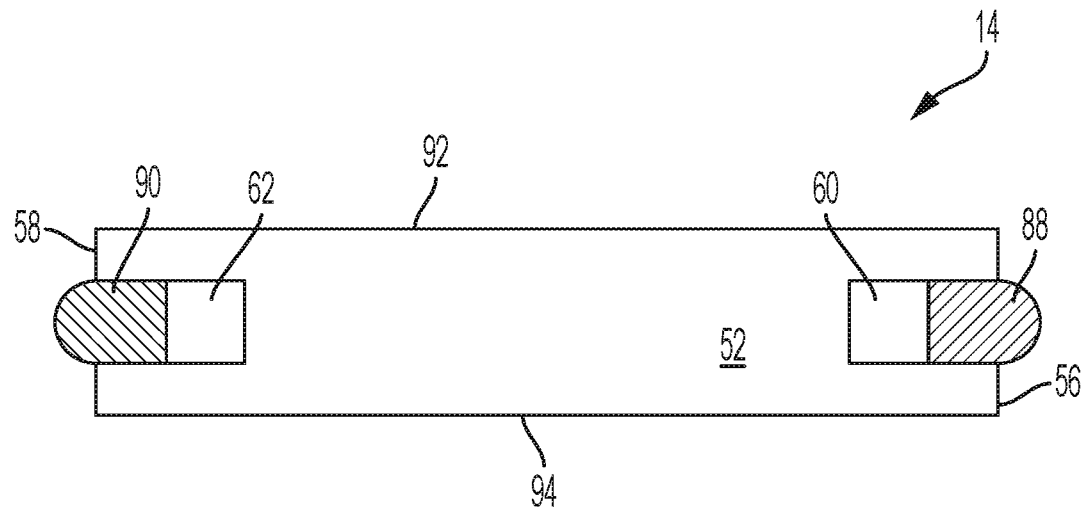
Figure 17:
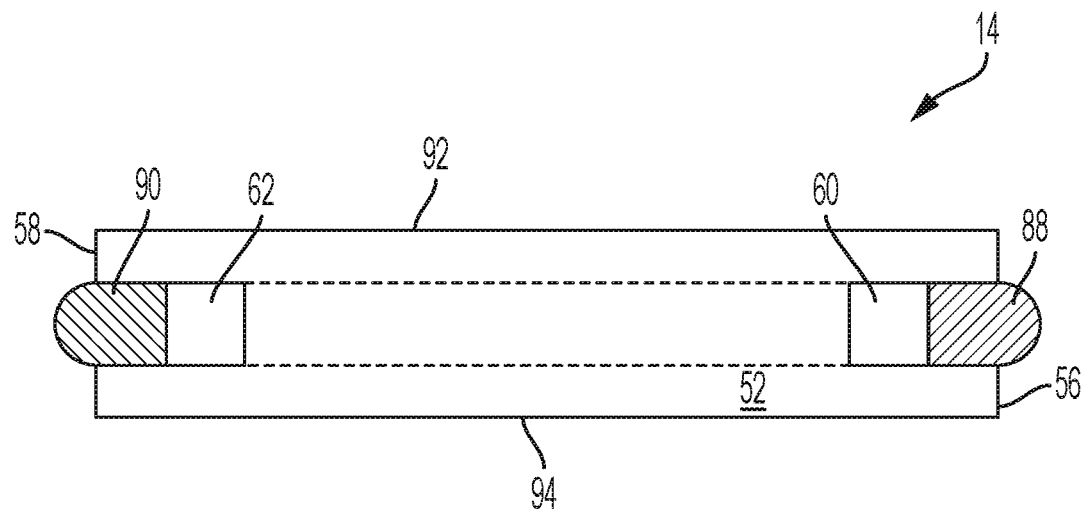

FIGS. 14-17 illustrate examples of grasp regions on fastening members 14. It is to be understood, as mentioned above, that only one grasp region may be provided on a fastening member. It is also to be understood that the fastening members 14 of FIGS. 14-17 may also be shaped (i.e., not rectangular), for example, like FIGS. 11-13, or otherwise shaped. In FIGS. 14-17, the grasp regions are illustrated as cross-hashed areas for ease in illustration. Referring to FIG. 14, the grasp regions 88 and 90 are illustrated adjacent to the first end 56 and the second end 58, respectively. In such an example, the grasp regions 88, 90 are positioned fully laterally outboard of the first and second fasteners 60, 62 and extend fully intermediate the first side edge 92 and the second side edge 94, but may also extend partially intermediate the first side edge 92 and the second side edge 94. Referring to FIG. 15, the first grasp region 88 is illustrated intermediate the first end 56 and the first fastener 60 and the second grasp region 90 is illustrated intermediate the second end 58 and the second fastener 62. In such a configuration, the grasp regions 88 and 90 are illustrated as only extending partially intermediate the first side edge 92 and the second side edge 94, but could also extend fully intermediate the first side edge 92 and the second side edge 94. Also, in FIG. 15, the grasp regions 88 and 90 are illustrated as being fully laterally outboard of the first and second fasteners 60, 62, but could also extend under, or at least partially under, the first and second fasteners 60, 62. Referring to FIG. 16, the first grasp region 88 is illustrated extending laterally outwardly from the first fastener 60 and beyond the first end 56 and the second grasp region 90 is illustrated extending laterally outwardly from the second fastener 62 and beyond the second end 58. In such a configuration, the grasp regions 88 and 90 extend only partially intermediate the first side edge 92 and the second side edge 94, but could also extend fully intermediate the first side edge 92 and the second side edge 94. Also, in FIG. 16, the grasp regions 88 and 90 are illustrated as being fully laterally outboard of the first and second fasteners 60, 62, but could also extend under, or at least partially under, the first and second fasteners 60, 62. The portions of the grasp regions 88, 90 that extend beyond the first end 56 and the second end 58, respectively, may comprise any suitable shape. For instance, these portions may comprise one or more curvilinear portions or one or more concave or convex portions to avoid any sharp corners for protection of a wearer's skin. Referring to FIG. 17, the material comprising the grasp regions 88, 90 may comprise a single piece or strip of material that may extend along the entire length of the fastening member 14, or portions thereof, and beyond the first end 56 and second end 58. The single piece or strip of material may be positioned between the various layers or be positioned on one of the outer surfaces of the fastening members.

As mentioned above, the various grasp regions may have one or more different physical properties than a remainder of the fully removable fastening member (i.e., an area not in a grasp region or overlapping a fastener). The one or more different physical properties may be basis weight, texture, stiffness, thickness, coefficient of friction, number of layers or materials, and/or other physical properties discussed herein. These one or more physical properties may aid in allowing a nurse or caregiver to easily grip the grasp regions during repositioning of the fastening members and/or during absorbent article changes. In addition, the grasp regions may have a different color or shade of the same color (e.g., dark blue and light blue) as the remainder of the fully removable fastening member and/or the fasteners. The color differential in the grasp regions may aid a nurse or caregiver in quickly locating the grasp regions during repositioning of the fastening member and/or during absorbent article changes.

The grasp regions of FIGS. 13-17 may be embossed and/or comprise three-dimensional projections to create greater textures or coefficients of friction in the grasp regions compared to a remainder of the fastening members in areas free of the fasteners.

Fold Over for Grasp Regions

One way to create thicker, higher basis weight, and/or stiffer grasp regions is to fold one or more of the first and second nonwoven materials of the fastening members 14 over themselves in the grasp regions. FIGS. 18-23 are schematic cross-sectional illustrations of grasp regions e.g., 88 and portions of the fastening members 14 laterally inboard of the grasp regions to show examples of how the grasp regions may have higher thickness, basis weight, and/or stiffness than a remainder of the fastening members 14 in areas free of the fasteners (e.g., area 89). Only one side of the fastening members 14 are illustrated in FIGS. 18-23, but it is to be understood that if a second grasp region is provided, it may be the same or similar to that illustrated. In other instances, the second grasp region may be different than the first grasp region. The folding over may be performed before or after the fasteners are attached, depending on the fold over configuration.

As discussed herein, the fastening members 14 may each comprise a first nonwoven material 100 forming the first surface 52 and a second nonwoven material 102 forming the second surface 54. An optional elastic material 104 may be positioned at least partially intermediate the first and second nonwoven materials 100 and 102. Fastener 60, 62 locations are also illustrated as examples. "W" means wearer-facing side and "G" means garment-facing side of the fastening members. The various layers of the fastening members may be joined together by adhesives and/or bonds, for example. In FIGS. 18-23, the elastic material 104 may optionally extend into the grasp region and/or be folded over as illustrated in dashed lines.

Figure 18:
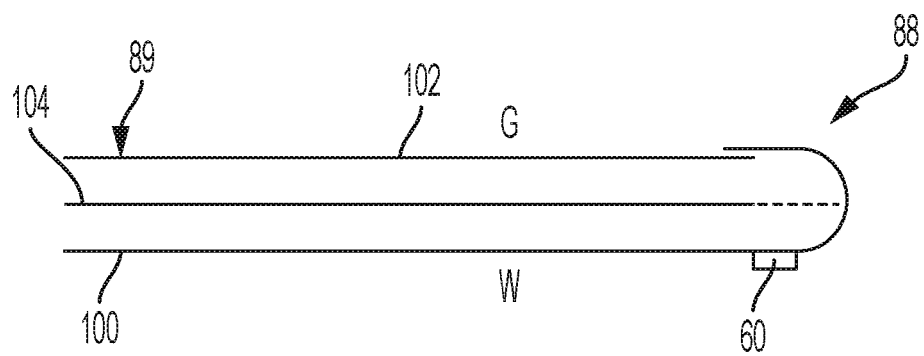
FIGS. 18-23 are plan views of one side of removable fastening members comprising fasteners and grasp regions, showing different fold over configurations in the grasp regions.
Figure 19:
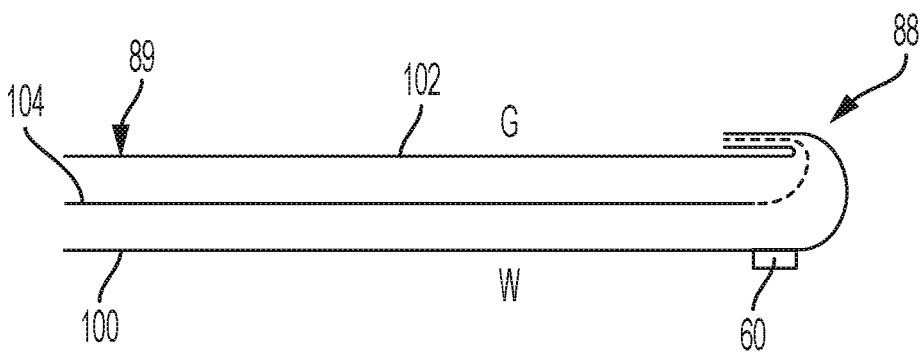
Figure 20:
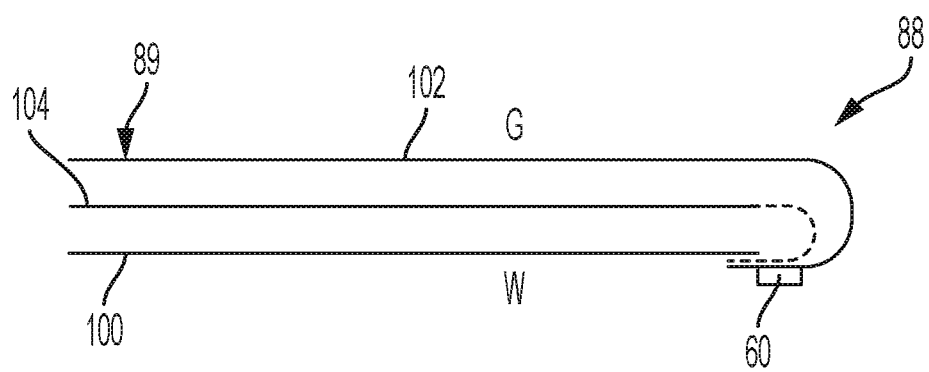
Figure 21:
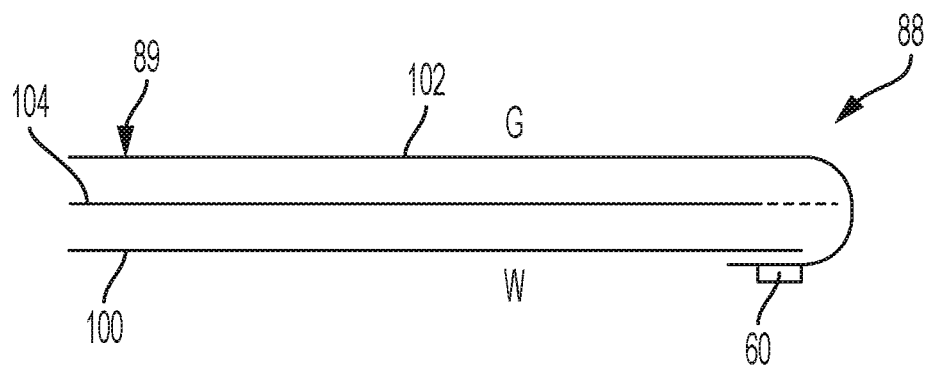
Figure 22:
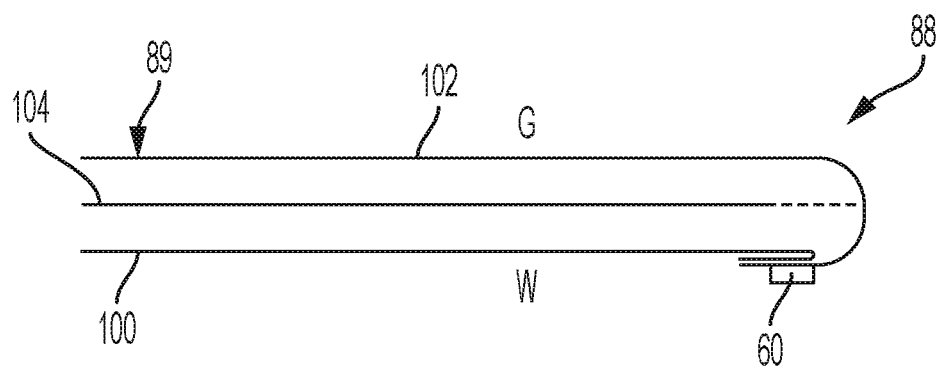
Figure 23:
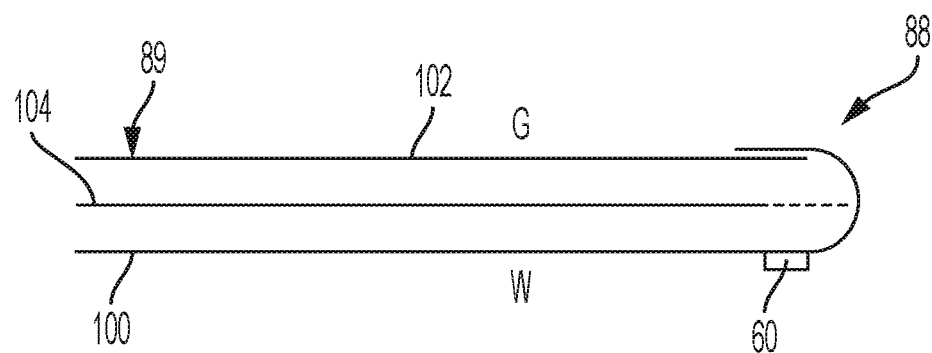

Referring to FIG. 18, the first nonwoven material 100 may extend laterally beyond the elastic material 104 and the second nonwoven material 102 may be folded over a portion of the second nonwoven material 102. In such an instance, the grasp region 88 is formed of two layers and has a higher basis weight, thickness, and stiffness than a single layer grasp region. Referring to FIG. 19, both the first and second nonwoven materials 100 and 102 may extend beyond the elastic material 104. The first nonwoven material 100 and may be folded over a portion of the second nonwoven material 102. The second nonwoven material 102 may be folded over a portion of itself. In such an instance, the grasp region 88 is formed of three layers and has a higher basis weight, thickness, and stiffness than a single layer grasp region. Referring to FIG. 20, the second nonwoven material 102 may extend laterally beyond the elastic material 104 and the first nonwoven material 102 and may be folded over a portion of the first nonwoven material 100. In such an instance, the grasp region 88 is formed of two layers and has a higher basis weight, thickness, and stiffness than a single layer grasp region. Referring to FIG. 21, both the first and second nonwoven materials 100 and 102 may extend beyond the elastic material 104. The second nonwoven material 100 and may be folded over a portion of the first nonwoven material 100. The first nonwoven material 100 may merely extend outwardly from the elastic material 104. In such an instance, the grasp region 88 may be formed of three layers thereby providing higher basis weight, thicker, and stiffer grasp regions compared to a one or two layer grasp region. Referring to FIG. 22, the first nonwoven material 100 may extend outwardly from the elastic material 104 and may be folded over a portion of itself. The second nonwoven material 102 may extend outwardly from the elastic material 104 and may be folded over a portion of the first nonwoven material 100. In such an instance, the grasp region 88 may be formed of three layers thereby providing higher basis weight, thicker, and stiffer grasp regions compared to a one or two layer grasp region. In some instances, the elastic material 104 may also extend outwardly from what is shown in FIGS. 18-23 and may or may not be folded over itself. In some instances, the elastic material 104 may form parts of the grasp regions.

The first and second nonwoven materials of FIGS. 18-23 may be embossed and/or comprise three-dimensional projections at least in the grasp regions to create greater textures or coefficients of friction in the grasp regions compared to a remainder of the fastening members in areas free of the fasteners.

Grasp Regions with Additional Materials

Figure 24:
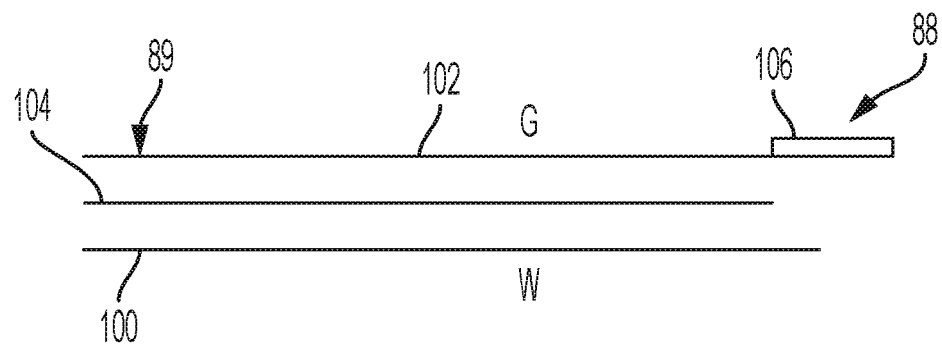
FIGS. 24-27 are plan views of one side of removable fastening members comprising fasteners and grasp regions, showing different configurations of the grasp regions with one or more additional materials.
Figure 25:
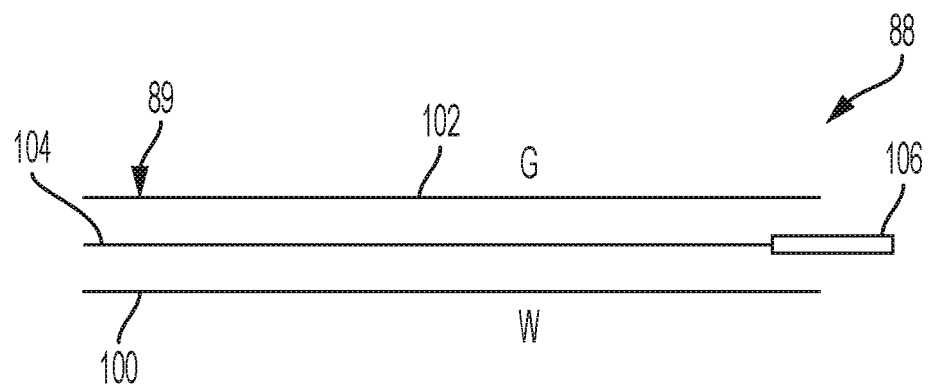
Figure 26:
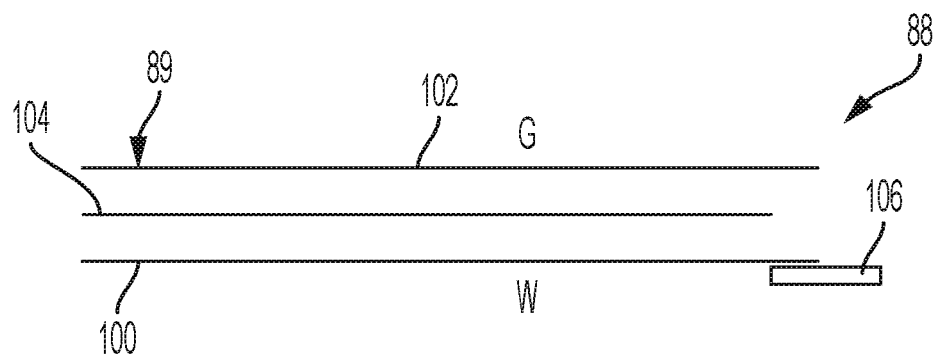
Figure 27:
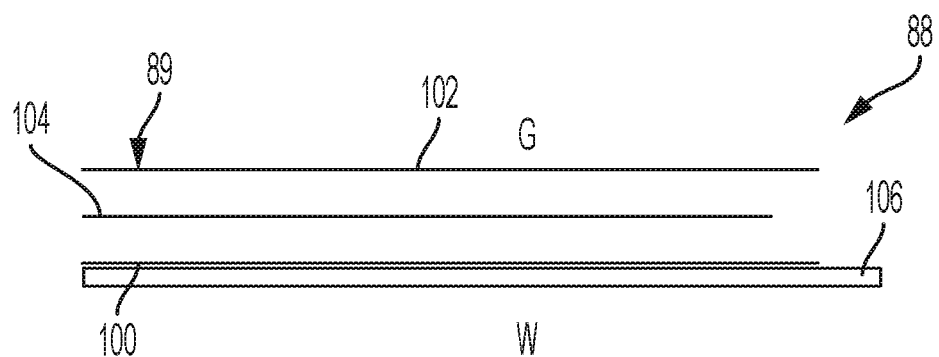

Instead of folding over one or more of the first and second nonwoven materials 100, 102 to create increased thickness, basis weight, and stiffness in the grasp regions, an additional material may be provided to accomplish the same or similar function. The additional material may comprise or be a nonwoven material, a film, an adhesive, and/or a foam, for example. The additional material may be a laminate of any combination of these materials or a laminate subjected to a solid-state formation process (e.g., where one layer is pushed through or exposed through another layer of the laminate). The additional material may also be a scrim or may be a material applied in a temporarily liquid state that subsequently becomes at least partially solid (e.g., adhesives, polyolefins, foams, and the like). The additional material may also be rearranged from a base material (e.g., via pleating, gathering, or melting). The additional material may be a solid (fiber or particle) embedded, entrapped, or otherwise held in the base material. This additional material may help in creating thicker, higher basis weight, and/or stiffer grasp regions. FIGS. 24-27 are schematic cross-sectional illustrations of grasp regions e.g., 88 and portions of the fastening members 14 laterally inboard of the grasp regions with one or more additional materials 106 to show examples of how the grasp regions may have higher basis weights, greater thickness, and/or be stiffer than a remainder of the fastening members 14 in areas free of the fasteners (e.g., area 89). The additional material 106 may be glued, bonded and/or otherwise attached to the first nonwoven material 100, the second nonwoven material 102, and/or the elastic material 104 in various different configurations. Referring to FIG. 24, the additional material 106 may be positioned on the garment-facing side "G". The additional material 106 may or may not extend laterally outwardly from the second nonwoven material 102. The additional material 106 may overlap with and/or be joined to the second nonwoven material 102. Referring to FIG. 25, the additional material 106 may be positioned intermediate the first and second nonwoven materials 100, 102. The additional material 106 may or may not extend laterally outwardly from the first nonwoven material 100 and/or from the second nonwoven material 102. The additional material 106 may overlap with and/or be joined to the elastic material 104, the first nonwoven material, and/or the second nonwoven material 102. Referring to FIG. 26, the additional material 106 may be positioned on the wearer-facing-facing side "W". The additional material 106 may or may not extend laterally outwardly from the first nonwoven material 100. The additional material 106 may overlap with and/or be joined to the first nonwoven material 100. Referring to FIG. 27, the additional material 106 may be positioned on the wearer-facing-facing side "W" and extend the entire lateral length of the fastening members (i.e., from the first end region to the second end region) or may extend only a portion of the entire lateral length of the fastening members. The additional material 106 may also extend laterally outwardly from the first and second nonwoven materials 100, 102 in the grasp regions 88, 90. The additional material 106 may overlap with and/or be joined to the first nonwoven material 100.

The additional material 106 may take on any of the configurations of the grasp regions 88, 90 illustrated in FIGS. 14-17, for example.

Fastener Shapes

Figure 37:
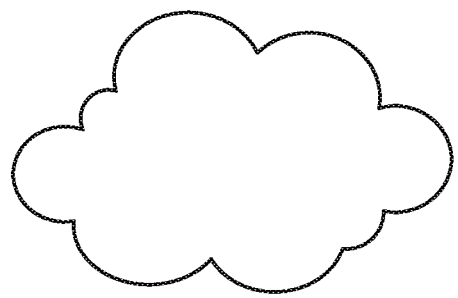
Figure 38:
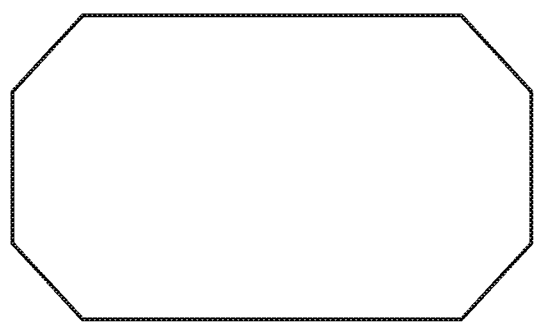

The first and second fasteners 60, 62 (see e.g., FIGS. 3 and 5-7) may have any suitable shapes and/or colors. It may be desirable to have the first and second fasteners 60, 62 to have a different color or a different shade of the same color (e.g., dark blue and light blue) than a remainder of the fastening members so the fasteners may easily be identified even in low-light settings. This helps nurses and/or caregivers perform a faster absorbent article change and/or repositioning thereby reducing stress on wearer babies. The first and second fasteners may be round (FIGS. 28, 31), heart shaped (FIGS. 29, 32, 35, and 36), ovate (FIGS. 30, 33), square (FIG. 34), rectangular, star shaped, triangular, cloud shaped (FIG. 37), a generally rectangular shape with somewhat rounded corners (FIG. 38), or any other suitable shape. A single fastening member may have two differently shaped fasteners. The first and second fasteners may be oriented as illustrated or may be positioned 90 degrees clockwise from that illustrated, 90 degrees counter-clockwise from that illustrated, or 180 degrees from that illustrated. For example, the fastener of FIG. 29 is illustrated positioned 90 degrees clockwise in FIG. 35 and is illustrated positioned 90 degrees counter-clockwise in FIG. 36. The fasteners may also be positioned less than 90 degrees clockwise or counter-clockwise from that shown or more than 90 degrees clockwise or counter-clockwise from that shown.

Referring to FIGS. 28-30 and 35-38, the fasteners may comprise hooks on a surface configured for engagement with loops of an outer cover nonwoven material or other portions of an absorbent article. In other instances, the fasteners may comprise loops and the outer cover nonwoven material may comprise hooks. Referring to FIGS. 31-34, only first portions 108 of the fasteners may comprise hooks with other second portions 110 of the fasteners not comprising hooks or being free of hooks. The second portions 110 may be formed by not extruding hooks in certain areas or by mechanical and/or thermal destruction of the hooks in the second portions 110, for example. In an instance, only the second portions 110 may comprise hooks and the first portions 108 may be free of hooks. The first portions 108 may be a different color or a different shade of the same color as the second portions 110.

Some advantages of having either first or second portions without hooks is the desire or need to: (1) have a region of the fastener with a different stiffness or folding behavior (e.g., more or less flexible) than another portion of the fastener to better conform to the wearer's anatomy; (2) have a region of the fastener that is less abrasive to the wearer's skin than another portion of the fastener; (3) have a delineated transition between a hook region and a hook-free region to aid in mechanical advantage when grasping or to provide a signal of where to grasp the fastener; (4) make portions of the fastener adhere less aggressively to a second fastening substrate (easy start to removal), and/or (5) have edges or corners be more flexible then another portion of the fastener to prevent, or at least inhibit, the edges or corners from poking through the substrate fastener material and irritating a wearer's skin.

As an example, the fastener of FIG. 31 may have a lower bending modulus than FIG. 28. This may allow the fastener and fastening member to fit more comfortable regardless of what positioned the baby may be in. For example, a baby in the prone positioned (with legs pulled up) may have increased bend in the waist region and the lower bending modulus of the fastener may allow the fastener and fastening member to better conform to the baby's shape.

Fastening Belt

Figure 39:
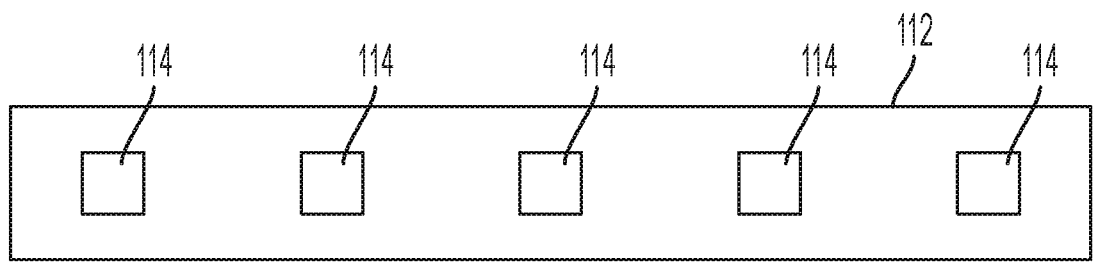
FIG. 39 is a plan view of a fastening belt comprising a plurality of fasteners.

Instead of providing one or two fastening members 14, a fastening belt may be provided with the chassis 12. An example fastening belt 112 with a plurality of fastening members 114 is illustrated in FIG. 39. A single fastening belt 112 may be provided with the chassis 12. The fastening belt 112 may have any suitable number of fasteners 114, such as two, three, four, five, six, seven, eight, nine, or ten, for example. The fastening belt 112 may wrap fully or partially around a wearer's waist circumference. The fastening belt 112 may even wrap fully around itself and then overlap portions of itself, up to, for example, 50% of itself. The fasteners 114 in the middle portion of the fastening belt 112 may engage portions of the outer cover nonwoven material of the chassis 12 in side waist regions, back waist regions, or front waist regions, for example, to maintain the fastening belt 112 in correct position on a wearer (much like a belt through belt loops in a pair of pants). The fastening belt 112 may be particularly suited for smaller absorbent articles having the size ranges disclosed herein. The fastening belt 112, in some instances, may merely be formed of two individual fastening members 14 with a fastener of one fastening member overlapped by a portion a garment facing sided of the other fastening member 14, thereby forming a fastening belt with three fasteners on the wearer-facing side.

Shaped Fastening Members

As referenced above, the fastening members 14 of the present disclosure may be shaped (i.e., not rectangular in their outer perimeter). In a rectangular fastening member configuration, the nurses or caregivers are somewhat limited in how he or she can apply the fastening members to fit a certain wearer. Wearers are many different sizes and shapes. The present disclosure provides absorbent articles with one or more fully removable, shaped fastening members comprising fasteners (e.g., hooks) that provide nurses and caregivers with more customizable options for absorbent article fit. The fully removable shaped fastening members may have first and second side edges at least one or both with one or more curvilinear portions or one or more concave and/or convex portions. The fully removable fastening members may each have a central longitudinal axis and a central longitudinal axis. The first and second side edges may be symmetrical or asymmetrical to each other about the central lateral axis. End edges of the fastening members may also be shaped, comprise one or more curvilinear portions, and/or comprise one or more convex or concave portions. The first and second end edges of the fastening member may be symmetrical or asymmetrical to each other about the central longitudinal axis. In other instances, the shaped fastening members may not have side edges and/or end edges with one or more convex or concave portions or curvilinear portions, but may still be shaped fastening members, as will be discussed in further detail below.

Referring to FIGS. 40-52, a fastening member 14 may have a first end 56, a second end 58, a first side edge 92, and a second side edge 94. The fastening members 14 may have a central lateral axis 82 and a central longitudinal axis 100. The fastening members 14 may comprise a first fastener 60 and a second fastener 62. The first and second fasteners 60, 62 may have any of the fastener configurations disclosed herein. With the exception of FIGS. 43 and 47, the fastening members 14 may each have one curvilinear portion, concave portion, and/or convex portion on the first end 56, the second end 58, the first side edge 92, and/or the second side edge 94. The fastening members of FIGS. 40-52 also illustrate examples of grasp regions 88, 90 in various configurations. It is noted that the grasp regions 88, 90 may also be shaped or have shaped portions on their laterally inboard side or elsewhere. It is also to be noted that the grasp regions 88, 90 may have any of the features discussed herein, such as fold over or additional materials, for example.

Figure 40:
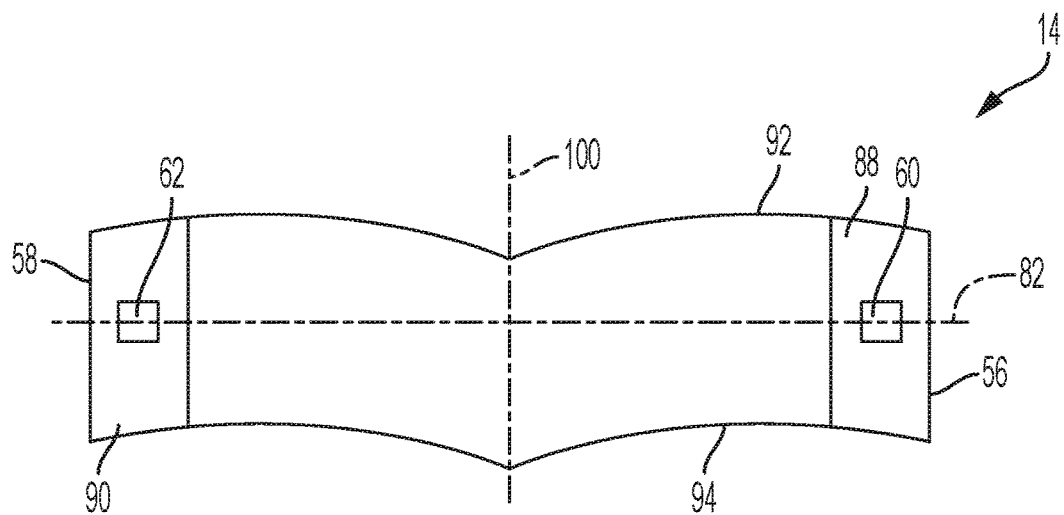
FIGS. 40-52 are plan views of shaped fastening members of the present disclosure.

FIG. 40 illustrates a plan view of a fastening member 14. The first side edge 92 comprises two convex portions relative to the central lateral axis 82. The second side edge 94 comprises two concave portions relative to the central lateral axis 82. The fastening member 14 is asymmetric about the central lateral axis 82. The first and second ends 56, 58 are linear, but may also comprise one or more curvilinear portions. The fastening member 14 is symmetrical about the central longitudinal axis 100.

Figure 41:
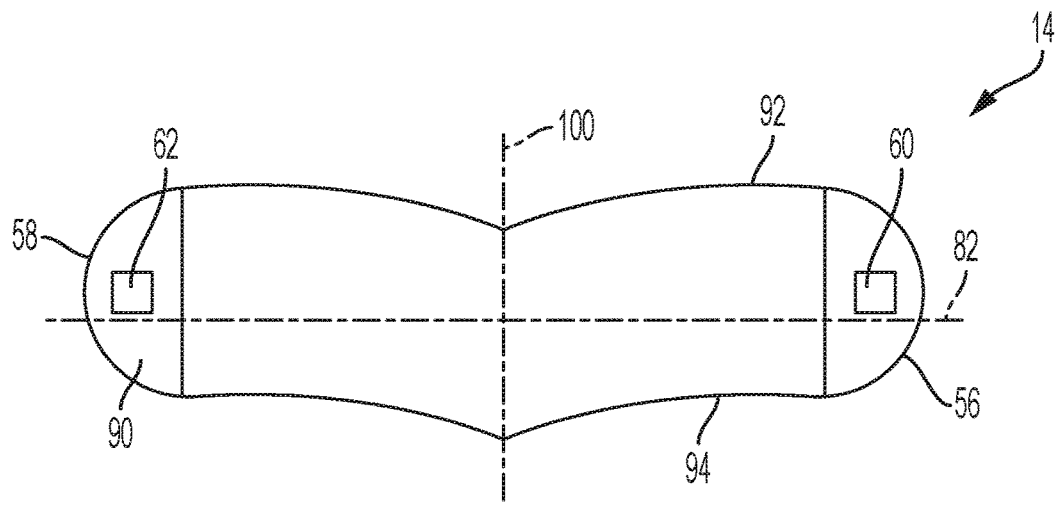

FIG. 41 illustrates a plan view of a fastening member 14. The first side edge 92 comprises two convex portions relative to the central lateral axis 82. The second side edge 94 comprises two concave portions and two convex portions both relative to the central lateral axis 82. The fastening member 14 is asymmetric about the central lateral axis 82. The first and second ends 56, 58 each comprise a convex or curvilinear portion relative to the central longitudinal axis 100. The fastening member 14 is symmetrical about the central longitudinal axis 100.

Figure 42:
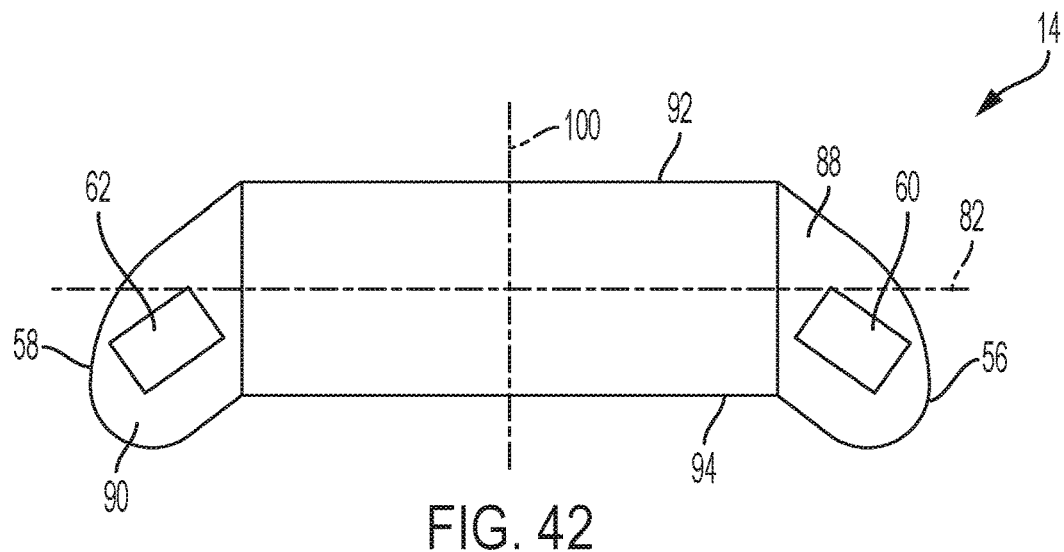

FIG. 42 illustrates a plan view of a fastening member 14. The first side edge 92 comprises a linear portion and two curvilinear portions. The second side edge 94 comprises a linear portion and two curvilinear portions. The fastening member 14 is asymmetric about the central lateral axis 82. The first and second ends 56, 58 each comprise a curvilinear portion. The fastening member 14 is symmetrical about the central longitudinal axis 100.

Figure 43:
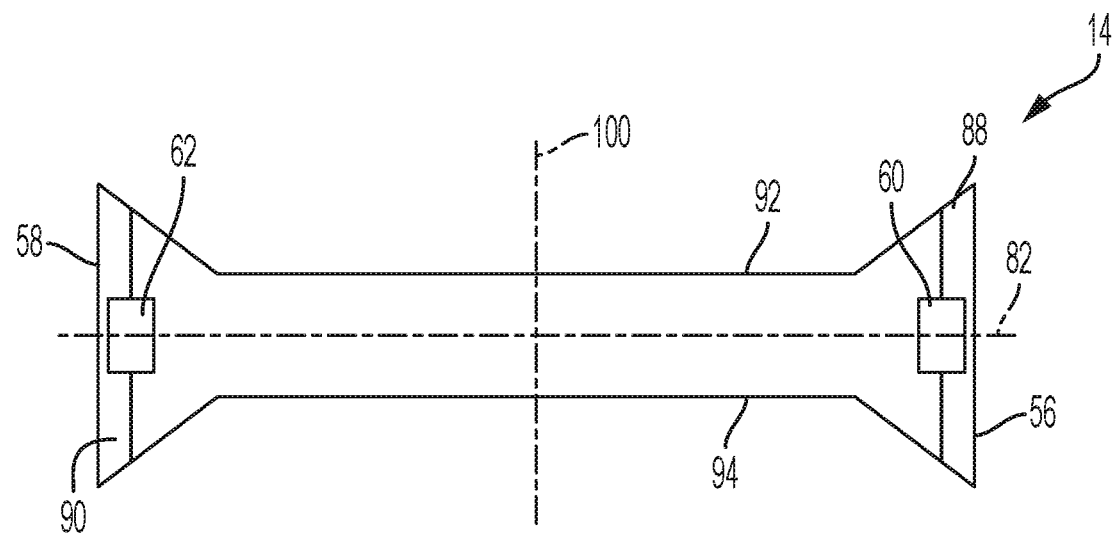

FIG. 43 illustrates a plan view of a fastening member 14. The first side edge 92 comprises 3 linear portions. The second side edge 94 comprises 3 linear portions. The fastening member 14 is symmetric about the central lateral axis 82. The first and second ends 56, 58 each comprise a linear portion. The fastening member 14 is symmetrical about the central longitudinal axis 100.

Figure 44:
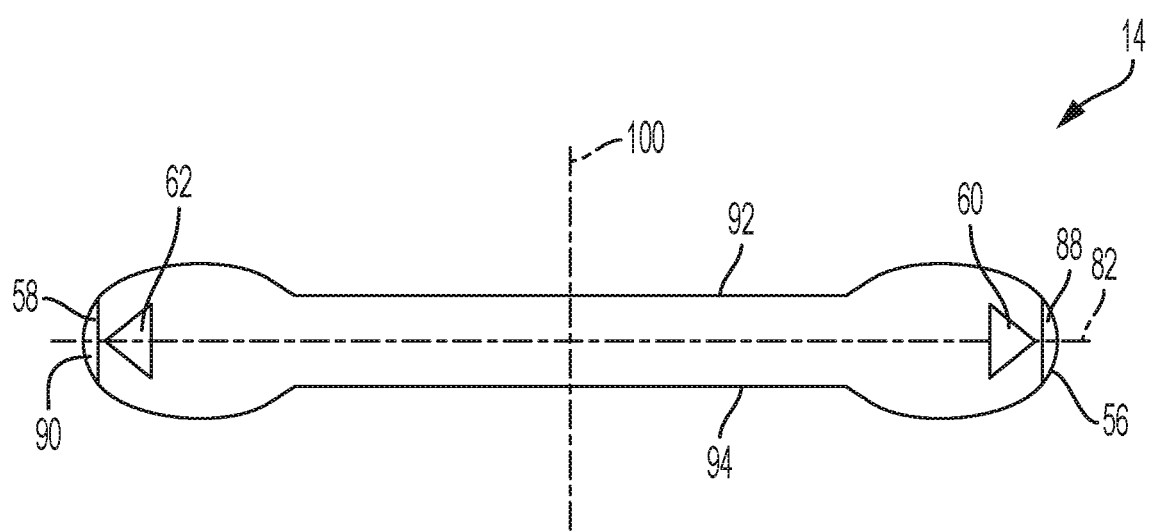

FIG. 44 illustrates a plan view of a fastening member 14. The first side edge 92 comprises a linear portion and two convex or curvilinear portions relative to the central lateral axis 82. The second side edge 94 comprises a linear portion and two convex or curvilinear portions relative to the central lateral axis 82. The fastening member 14 is symmetric about the central lateral axis 82. The first and second ends 56, 58 each comprise a convex or curvilinear portion relative to the central longitudinal axis 100. The fastening member 14 is symmetrical about the central longitudinal axis 100.

Figure 45:
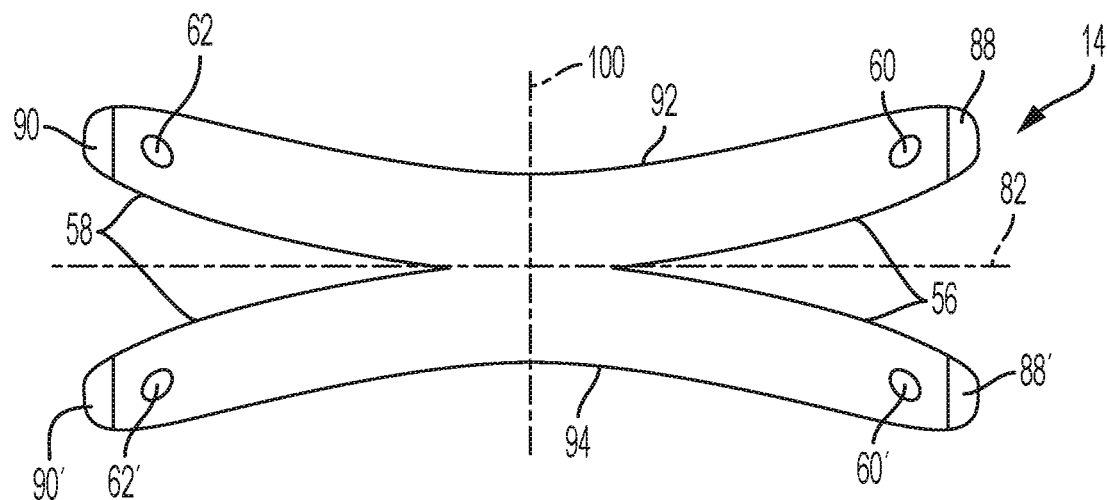

FIG. 45 illustrates a plan view of a fastening member 14. The first side edge 92 is concave with respect to the central lateral axis 82. The second side edge 94 is concave with respect to the central lateral axis 82. The fastening member 14 is symmetric about the central lateral axis 82. The first and second ends 56, 58 each comprise linear and curvilinear portions. The fastening member 14 is symmetrical about the central longitudinal axis 100. The fastening member has additional fasteners 60' and 62' and additional grasp regions 88' and 90'.

Figure 46:
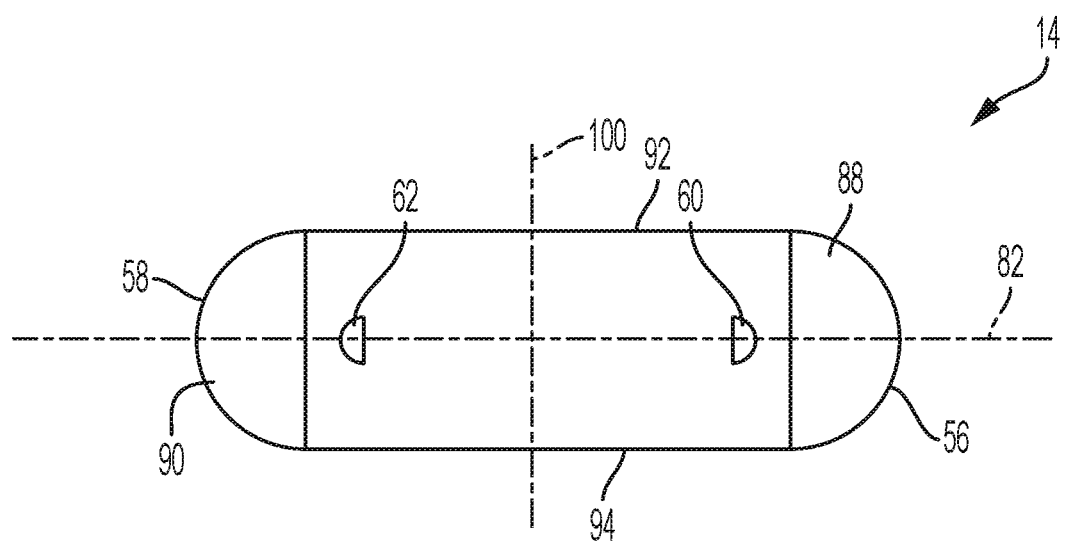

FIG. 46 illustrates a plan view of a fastening member 14. The first side edge 92 is linear. The second side edge 94 is linear. The fastening member 14 is symmetric about the central lateral axis 82. The first and second ends 56, 58 each comprise a convex or curvilinear portion relative to the central longitudinal axis 100. The fastening member 14 is symmetrical about the central longitudinal axis 100.

Figure 47:
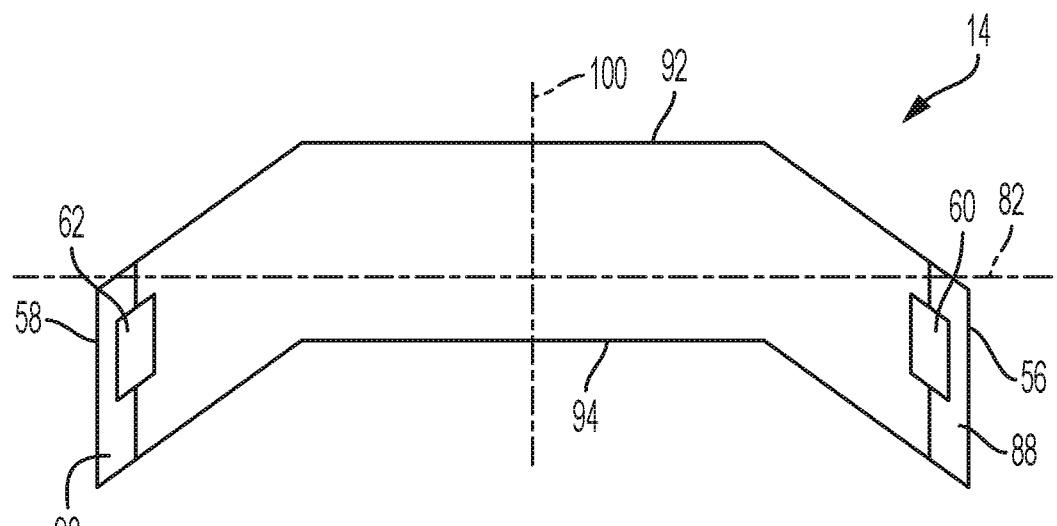

FIG. 47 illustrates a plan view of a fastening member 14. The first side edge 92 comprises 3 linear portions. The second side edge 94 comprises three linear portions. The fastening member 14 is asymmetric about the central lateral axis 82. The first and second ends 56, 58 each comprise a linear portion. The fastening member 14 is symmetrical about the central longitudinal axis 100.

Figure 48:
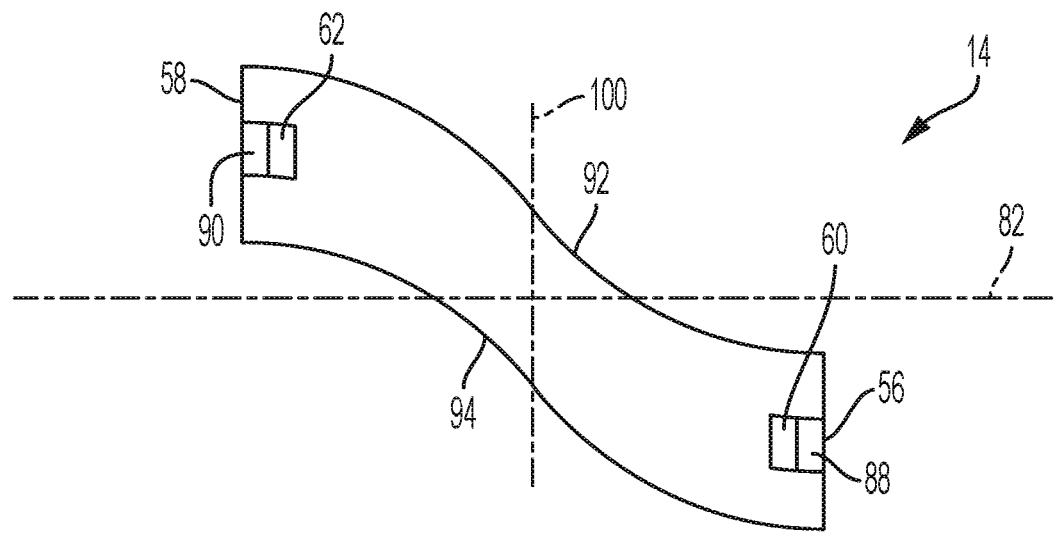

FIG. 48 illustrates a plan view of a fastening member 14. The first side edge 92 comprises multiple curvilinear portions. The second side edge 94 comprises multiple curvilinear portions. The fastening member 14 is asymmetric about the central lateral axis 82. The first and second ends 56, 58 each comprise a linear portion. The fastening member 14 is asymmetrical about the central longitudinal axis 100.

Figure 49:
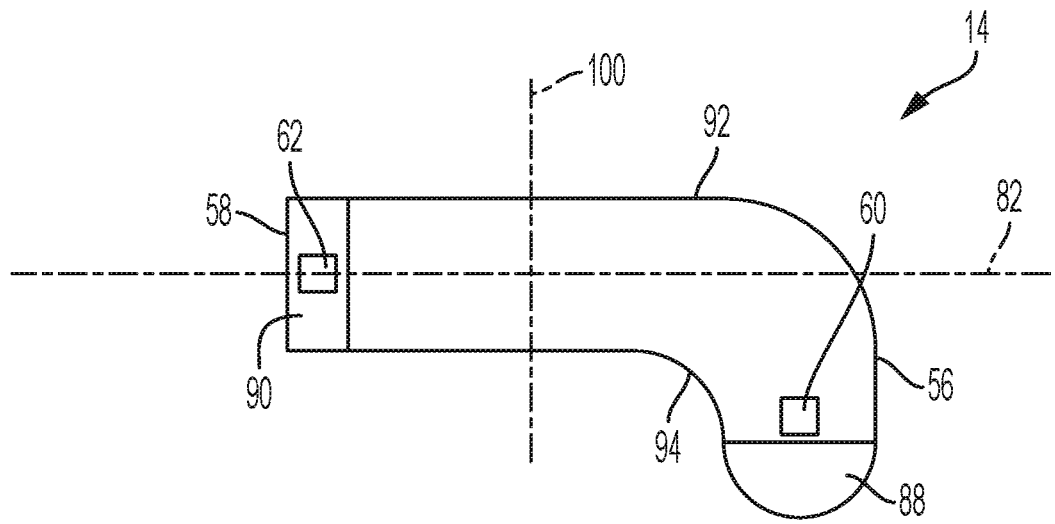

FIG. 49 illustrates a plan view of a fastening member 14. The first side edge 92 comprises a linear portion and a curvilinear portion. The second side edge 94 comprises a linear portion and multiple curvilinear portions. The fastening member 14 is asymmetric about the central lateral axis 82. The first end 56 comprises a linear portion. The second end 58 comprises a curvilinear portion. The fastening member 14 is asymmetrical about the central longitudinal axis 100.

Figure 50:
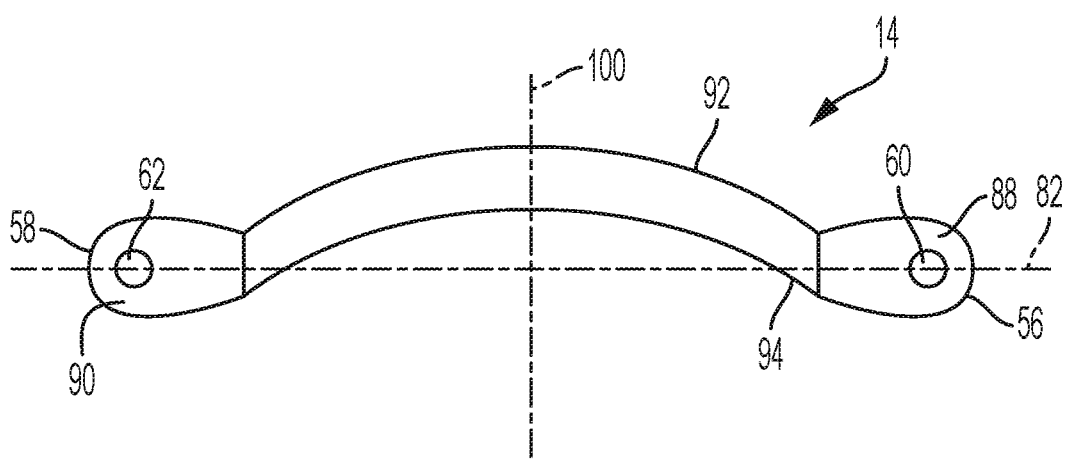

FIG. 50 illustrates a plan view of a fastening member 14. The first side edge 92 comprises three convex or curvilinear portions relative to the central lateral axis 82. The second side edge 94 comprises concave and convex portions relative to the central lateral axis 82. The fastening member 14 is asymmetric about the central lateral axis 82. The first and second ends 56, 58 each comprise a convex or curvilinear portion relative to the central longitudinal axis 100. The fastening member 14 is symmetrical about the central longitudinal axis 100.

Figure 51:
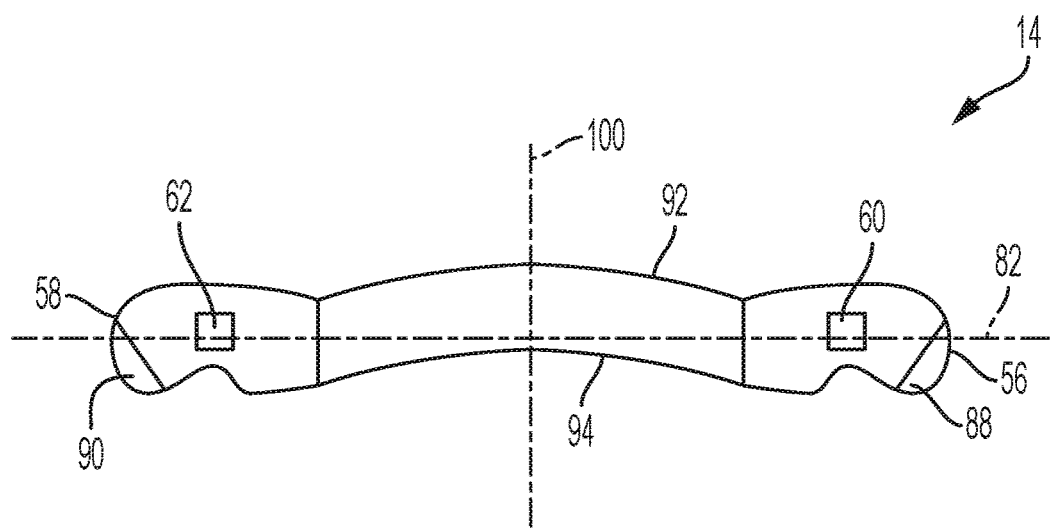

FIG. 51 illustrates a plan view of a fastening member 14. The first side edge 92 comprises three convex or curvilinear portions relative to the central lateral axis 82. The second side edge 94 comprises multiple concave and convex portions relative to the central lateral axis 82. The fastening member 14 is asymmetric about the central lateral axis 82. The first and second ends 56, 58 each comprise a convex or curvilinear portion relative to the central longitudinal axis 100. The fastening member 14 is symmetrical about the central longitudinal axis 100.

Figure 52:
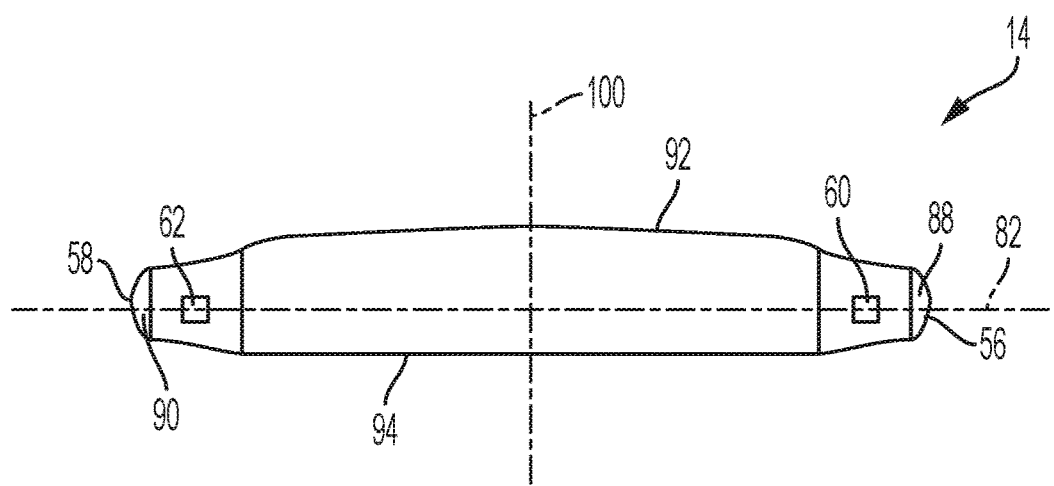

FIG. 52 illustrates a plan view of a fastening member 14. The first side edge 92 comprises a linear portion and multiple curvilinear portions. The second side edge 94 comprises a linear portion and multiple curvilinear portions. The fastening member 14 is asymmetric about the central lateral axis 82. The first and second ends 56, 58 each comprise a convex or curvilinear portion relative to the central longitudinal axis 100. The fastening member 14 is symmetrical about the central longitudinal axis 100.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited herein, including any cross referenced or related patent, patent publication, or patent application, is hereby incorporated by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular forms of the present disclosure have been illustrated and described, those of skill in the art will recognize that various other changes and modifications can be made without departing from the spirit and scope of the invention. It is therefore intended to cover in the appended claims all such changes and modifications that are within the scope of the present disclosure.

What is claimed is:

1. An absorbent article comprising:
   a topsheet;
   a backsheet;
   an absorbent core positioned at least partially between the topsheet and the backsheet;
   a first waist region;
   a second waist region;
   a crotch region extending between the first waist region and the second waist region;
   an outer cover nonwoven material joined to the backsheet and forming a portion of a garment-facing surface of the absorbent article; and
   a fully removable fastening member configured to join a portion of the first waist region to a portion of the second waist region, the fully removable fastening member comprising:
      a central lateral axis;
      a central longitudinal axis;
      a first side edge;
      a second side edge;
      a first nonwoven material comprising a first surface;
      a second nonwoven material comprising a second surface opposite to the first surface;
      an elastic film positioned at least partially between the first nonwoven material and the second nonwoven material;
      a first end region comprising a first end;
      a second end region comprising a second end, wherein the first end region is opposite to the second end region;
      a first fastener on the first surface and positioned in the first end region;
      a second fastener on the first surface and positioned in the second end region; and
      a grasp region either partially laterally outboard of the first fastener or laterally outboard of the first fastener in the first end region and proximate to the first end, wherein the grasp region is at least partially free of the elastic film.

2. The absorbent article of claim 1, wherein the grasp region comprises a folded over portion of the first end region.

3. The absorbent article of claim 1, wherein the grasp region comprises an additional material not present in a remainder of the first end region.

4. The absorbent article of claim 1, wherein the grasp region has a greater stiffness than a stiffness of a remainder of the fastening member outside of an area of overlap with the first fastener.

5. The absorbent article of claim 1, wherein the fully removable fastening member comprises a line of discontinuity, wherein the line of discontinuity separates the grasp region from a remainder of the fully removable fastening member.

6. The absorbent article of claim 5, wherein the line of discontinuity comprises a fold line, an adhesive, an overlap of two or more materials, a basis weight difference, a stiffness difference, or a color difference.

7. The absorbent article of claim 1, comprising:
   a second fully removable fastening member configured to join a second portion of the first waist region to the second waist region, the fully removable fastening member comprising:
      a third nonwoven material comprising a third surface;

a fourth nonwoven material comprising a fourth surface opposite to the third surface;

a third end region comprising a third end;

a fourth end region comprising a fourth end, wherein the third end region is opposite to the fourth end region;

a third fastener on the third surface and positioned in the third end region; and a fourth fastener on the third surface and positioned in the fourth end region.

8. The absorbent article of claim 1 comprising an acquisition material disposed at least partially between the topsheet and the absorbent core.

9. The absorbent article of claim 1 comprising a first waist edge, wherein the first waist edge comprises a first curvilinear portion.

10. The absorbent article of claim 9 comprising a second waist edge, wherein the second waist edge comprises a second curvilinear portion.

11. The absorbent article of claim 10, wherein the first waist edge and the second waist edge are substantially symmetrical about an absorbent article central lateral axis.

12. An absorbent article comprising:

a topsheet;

a backsheet;

an absorbent core positioned at least partially between the topsheet and the backsheet;

a first waist region;

a second waist region;

a crotch region extending between the first waist region and the second waist region;

an outer cover nonwoven material joined to the backsheet and forming a portion of a garment-facing surface of the absorbent article; and a fully removable fastening member comprising:
a central lateral axis;
a central longitudinal axis;
a first side edge;
a second side edge;
a first nonwoven material comprising a first surface;
a second nonwoven material comprising a second surface opposite to the first surface;
an elastic film positioned at least partially between the first nonwoven material and the second nonwoven material;
a first end region comprising a first end;
a second end region comprising a second end, wherein the first end region is opposite to the second end region;
a first fastener on the first surface and positioned in the first end region;
a second fastener on the first surface and positioned in the second end region; and
a grasp region proximate to the first end, wherein the grasp region is at least partially free of the elastic film, and wherein the grasp region extends at least partially under the first fastener.

13. The absorbent article of claim 12, wherein the first fastener is fully overlapped by the grasp region such that the grasp region extends laterally outboard and laterally inboard of the first fastener.

14. The absorbent article of claim 12, wherein the first side edge and the second side edge of the fully removable fastening member are symmetrical about the fully removable fastening member central lateral axis.

15. The absorbent article of claim 12, wherein the grasp region extends an entire length of the fully removable fastening member.

16. The absorbent article of claim 12, wherein the first fastener and the second fastener are a different color than a remainder of the fully removable fastening member.

17. An absorbent article comprising:

a topsheet;

a backsheet;

an absorbent core positioned at least partially between the topsheet and the backsheet;

a first waist region;

a second waist region;

a crotch region extending between the first waist region and the second waist region;

an outer cover nonwoven material joined to the backsheet and forming a portion of a garment-facing surface of the absorbent article; and a fully removable fastening member comprising:
a central lateral axis;
a central longitudinal axis;
a first side edge;
a second side edge;
a first nonwoven material comprising a first surface;
a second nonwoven material comprising a second surface opposite to the first surface;
an elastic film positioned at least partially between the first nonwoven material and the second nonwoven material;
a first end region comprising a first end;
a second end region comprising a second end, wherein the first end region is opposite to the second end region;
a first fastener on the first surface and positioned in the first end region;
a second fastener on the first surface and positioned in the second end region;
a first grasp region either partially laterally outboard of the first fastener or laterally outboard of the first fastener in the first end region and proximate to the first end; and
a second grasp region either partially laterally outboard of the second fastener or laterally outboard of the second fastener in the second end region and proximate to the second end;
wherein the first grasp region and the second grasp region have a different physical property than a remainder of the fully removable fastening member.

18. The absorbent article of claim 17, wherein the first grasp region and/or the second grasp region is at least partially free of the elastic film.

19. The absorbent article of claim 17, wherein the first grasp region and the second grasp region have different basis weight than the remainder of the fully removable fastening member.

20. The absorbent article of claim 17, wherein the first grasp region and the second grasp region have a different thickness than the remainder of the fully removable fastening member.

\* \* \* \* \*